(12) United States Patent
Fukushima

(10) Patent No.: US 10,520,719 B2
(45) Date of Patent: Dec. 31, 2019

(54) IMAGE ACQUISITION DEVICE

(71) Applicant: OLYMPUS CORPORATION, Hachioji-shi, Tokyo (JP)

(72) Inventor: Ikutoshi Fukushima, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 86 days.

(21) Appl. No.: 15/861,602

(22) Filed: Jan. 3, 2018

(65) Prior Publication Data
US 2018/0120554 A1 May 3, 2018

Related U.S. Application Data

(63) Continuation of application No. PCT/JP2015/073593, filed on Aug. 21, 2015.

(51) Int. Cl.
*G02B 23/24* (2006.01)

(52) U.S. Cl.
CPC ................... *G02B 23/243* (2013.01)

(58) Field of Classification Search
CPC .... G02B 15/173; G02B 15/177; G02B 15/20; G02B 23/2415; G02B 23/243; G02B 23/2438; A61B 1/00096; A61B 1/00193; H04N 5/23296; G03B 2205/0046
See application file for complete search history.

(56) References Cited

U.S. PATENT DOCUMENTS

| | | |
|---|---|---|
| 6,632,172 B1 | 10/2003 | Igarashi |
| 2001/0004298 A1 | 6/2001 | Kobayashi |
| 2002/0082476 A1 | 6/2002 | Takahashi et al. |
| 2003/0125608 A1 | 7/2003 | Igarashi |

(Continued)

FOREIGN PATENT DOCUMENTS

| | | |
|---|---|---|
| EP | 3096168 A1 | 11/2016 |
| JP | 07261099 A | 10/1995 |

(Continued)

OTHER PUBLICATIONS

International Search Report (ISR) dated Nov. 17, 2015 issued in International Application No. PCT/JP2015/073593.

(Continued)

*Primary Examiner* — Obafemi O Sosanya
(74) *Attorney, Agent, or Firm* — Holtz, Holtz & Volek PC

(57) ABSTRACT

An image acquisition device including: an imaging optical system forming two images having parallax; and an element acquiring the parallax images, the imaging optical system includes: a first negative lens group having negative refractive power; a first positive lens group having positive refractive power; and a second positive lens group having positive refractive power, the first negative lens group includes two negative lens groups disposed side by side in the parallax direction and having central axes respectively, the first positive lens group is a common lens group having a single central axis, and light rays emitted from the negative lens groups pass therethrough, the second positive lens group includes two positive lens groups disposed side by side in the parallax direction and having central axes respectively and the first positive lens group includes a moving lens group moved along the central axis of the first positive lens group.

15 Claims, 29 Drawing Sheets

(56) References Cited

U.S. PATENT DOCUMENTS

| | | | |
|---|---|---|---|
| 2009/0096865 A1 | 4/2009 | McKinley | |
| 2013/0120646 A1* | 5/2013 | Mukai | G02B 15/12 348/360 |
| 2015/0219882 A1* | 8/2015 | Mogi | G02B 15/173 348/345 |
| 2016/0070094 A1 | 3/2016 | Togino | |
| 2016/0320606 A1 | 11/2016 | Togino | |

FOREIGN PATENT DOCUMENTS

| | | | |
|---|---|---|---|
| JP | 07294827 A | 11/1995 | |
| JP | 2001147382 A | 5/2001 | |
| JP | 2001166258 A | 6/2001 | |
| JP | 2003005096 A | 1/2003 | |
| JP | 2014160240 A | 9/2014 | |
| WO | 2014147856 A1 | 9/2014 | |
| WO | 2015107733 A1 | 7/2015 | |

OTHER PUBLICATIONS

Written Opinion dated Nov. 17, 2015 issued in International Application No. PCT/JP2015/073593.

\* cited by examiner

FIG. 6

NEAR POINT

Y-DIRECTION (a) IMAGE HEIGHT 0.4

(b) IMAGE HEIGHT 0.3

(c) IMAGE HEIGHT 0.2

(d) IMAGE HEIGHT 0.1

(e) IMAGE HEIGHT 0.0

(f) IMAGE HEIGHT -0.2

(g) IMAGE HEIGHT -0.4

——— C LINE (656.2700 NM)
---------- d LINE (587.5600 NM)
—·—·— F LINE (486.1300 NM)

FIG. 17

FAR POINT        X-DIRECTION (a) IMAGE HEIGHT 0.4     0.0015

−0.0015

(b) IMAGE HEIGHT 0.3     0.0015

−0.0015

(c) IMAGE HEIGHT 0.2     0.0015

−0.0015

(d) IMAGE HEIGHT 0.1     0.0015

−0.0015

(e) IMAGE HEIGHT 0.0     0.0015

−0.0015

(f) IMAGE HEIGHT −0.2    0.0015

−0.0015

(g) IMAGE HEIGHT −0.4    0.0015

−0.0015

——————— C LINE (656.2700 NM)
- - - - - - -  d LINE (587.5600 NM)
— - — - — -  F LINE (486.1300 NM)

FIG. 29
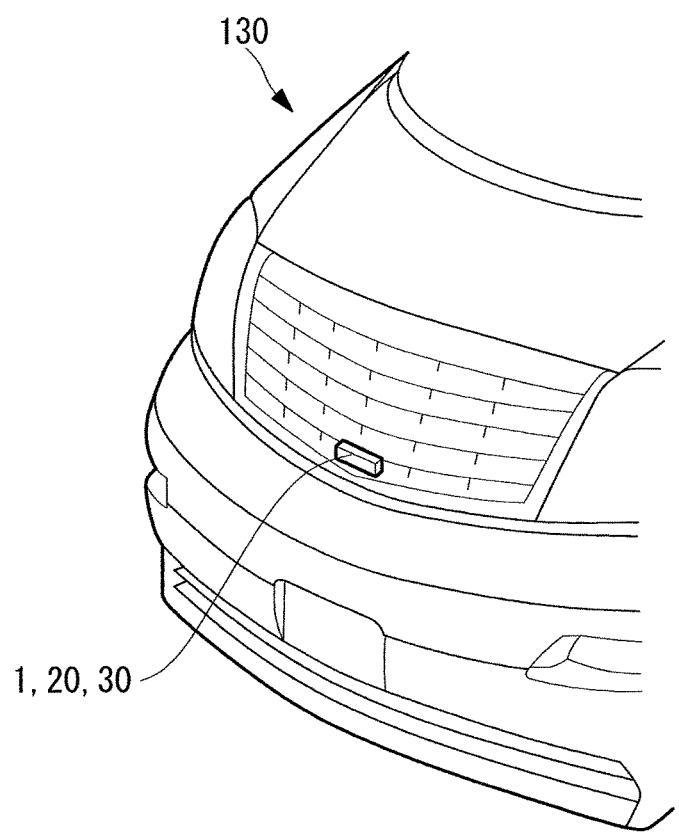
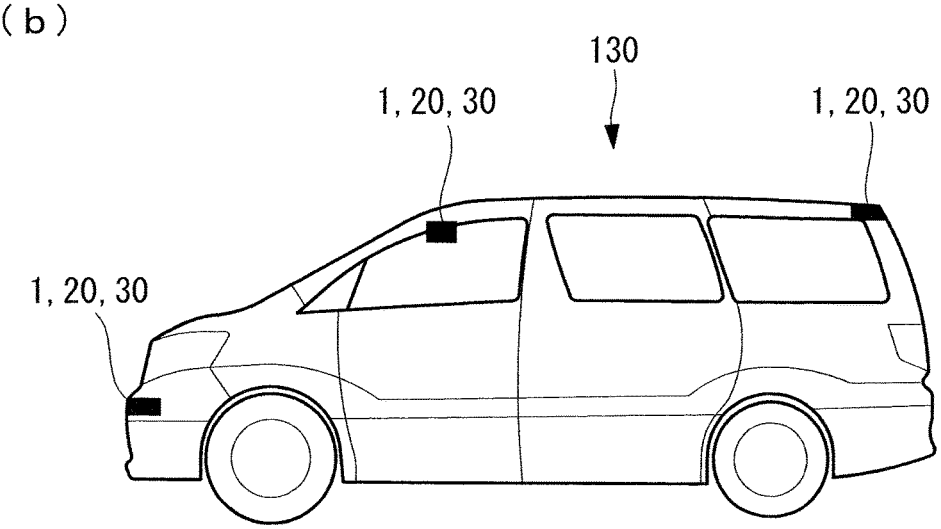

IMAGE ACQUISITION DEVICE

CROSS-REFERENCE TO RELATED APPLICATIONS

This is a Continuation Application of International Application No. PCT/JP2015/073593 filed on Aug. 21, 2015. The content of International Application No. PCT/JP2015/073593 is hereby incorporated herein by reference in its entirety.

TECHNICAL FIELD

The present invention relates to an image acquisition device.

BACKGROUND ART

There is a known stereoscopic imaging optical system in which two lens systems having different optical axes are disposed at a distal end thereof, in order to acquire parallax images required for stereoscopic viewing (for example, see PTL In this stereoscopic imaging optical system, one lens group is moved in the optical-axis direction in order to adjust the focal position on an object surface.

CITATION LIST

Patent Literature

{PTL 1} PCT International Publication No. WO 2014/147856

SUMMARY OF INVENTION

According to one aspect, the present invention provides an image acquisition device including: an imaging optical system that forms two images having parallax; and an image acquisition element that is disposed at an image side of the imaging optical system and that acquires the parallax images, wherein the imaging optical system is provided with a first negative lens group that has a negative refractive power, which are arranged in this order from an object side to an image side; a first positive lens group that has a positive refractive power, and a second positive lens group that has a positive refractive power; the first negative lens group is provided with two negative lens groups that are disposed side by side in a parallax direction corresponding to the parallax images and that have central axes respectively; the first positive lens group is a common lens group that has a single central axis and which light rays emitted from the respective negative lens groups in the first negative lens group to pass through; the second positive lens group is provided with two positive lens groups that are disposed side by side in the parallax direction corresponding to the parallax images and that have central axes respectively; and the first positive lens group is provided with a moving lens group that is moved along the central axis of the first positive lens group; wherein the image acquisition device further comprises an aperture stop that has openings corresponding to the respective parallax images and is disposed closer to an imaging surface than a lens surface of the first positive lens group, the lens surface being located closest to the first negative lens group; and central principal rays passing through the two negative lens groups reach the imaging surface without the principal rays intersecting.

BRIEF DESCRIPTION OF DRAWINGS

FIG. 6 is a view showing lateral aberrations of (a) the light ray L7, (b) the light ray L6, (c) the light ray L5, (d) the light ray L4, (e) the light ray L3, (f) the light ray L2, and (g) the light ray L1 in the Y-direction when the moving lens group in the imaging optical system shown in FIG. 3 is located at the near-point position shown in FIG. 2.

FIG. 17 is a view showing lateral aberrations of (a) the light ray L7, (b) the light ray L6, (c) the light ray L5, (d) the light ray L4, (e) the light ray L3, (f) the light ray L2, and (g) the light ray L1 in the X-direction when the moving lens group in the imaging optical system shown in FIG. 15 is located at the far-point position shown in FIG. 13.

FIG. 29 includes (a) a perspective view of a front portion of a vehicle to which the image acquisition device according to each of the embodiments is applied and (b) a side view thereof.

DESCRIPTION OF EMBODIMENTS

An image acquisition device 1 according to a first embodiment of the present invention will be described below with reference to the drawings.

Figure 1:
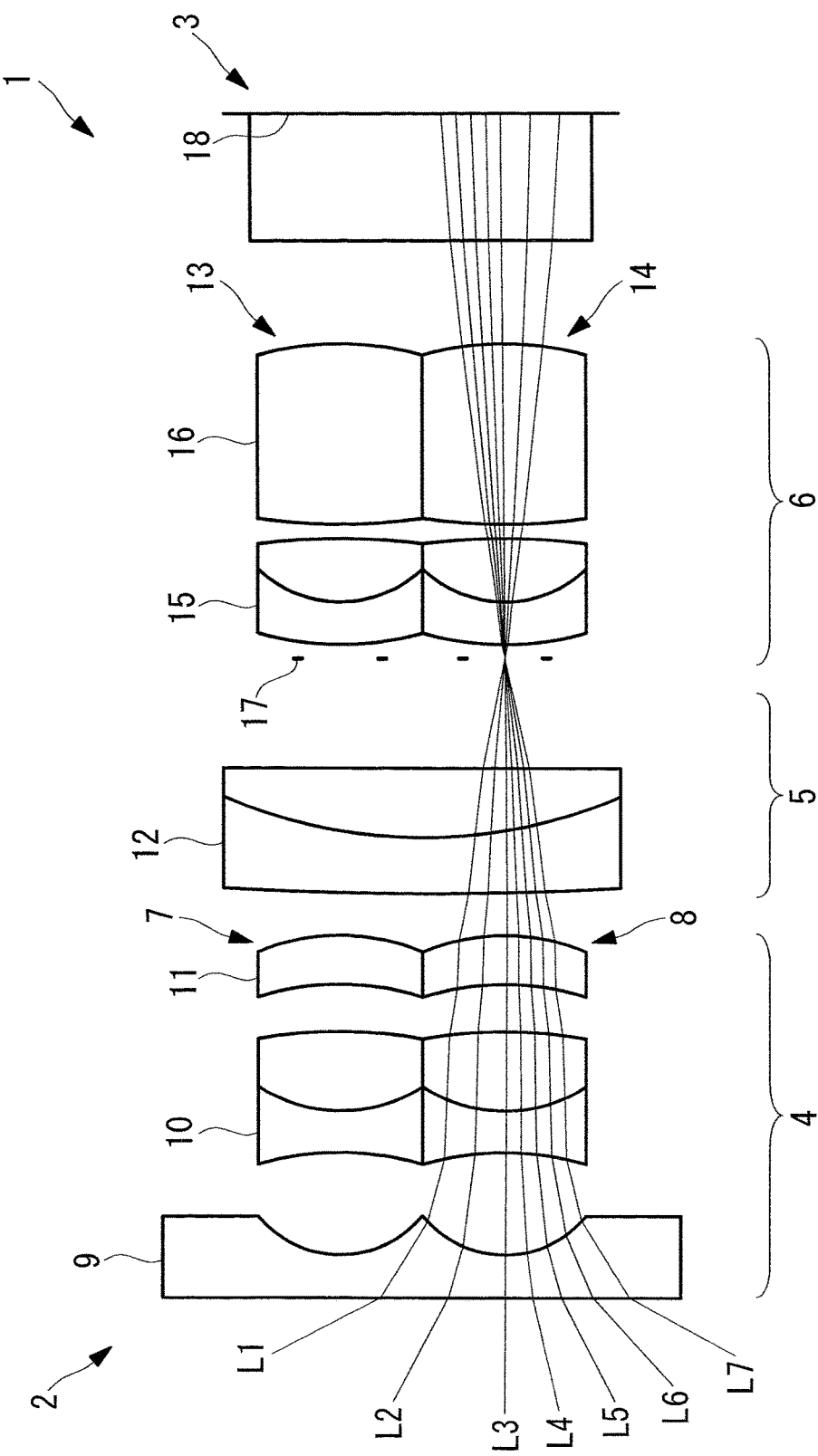
FIG. 1 is a view showing ray tracing of the principal ray when a moving lens group in an image acquisition device according to a first embodiment of the present invention is located at a far-point position.
Figure 2:
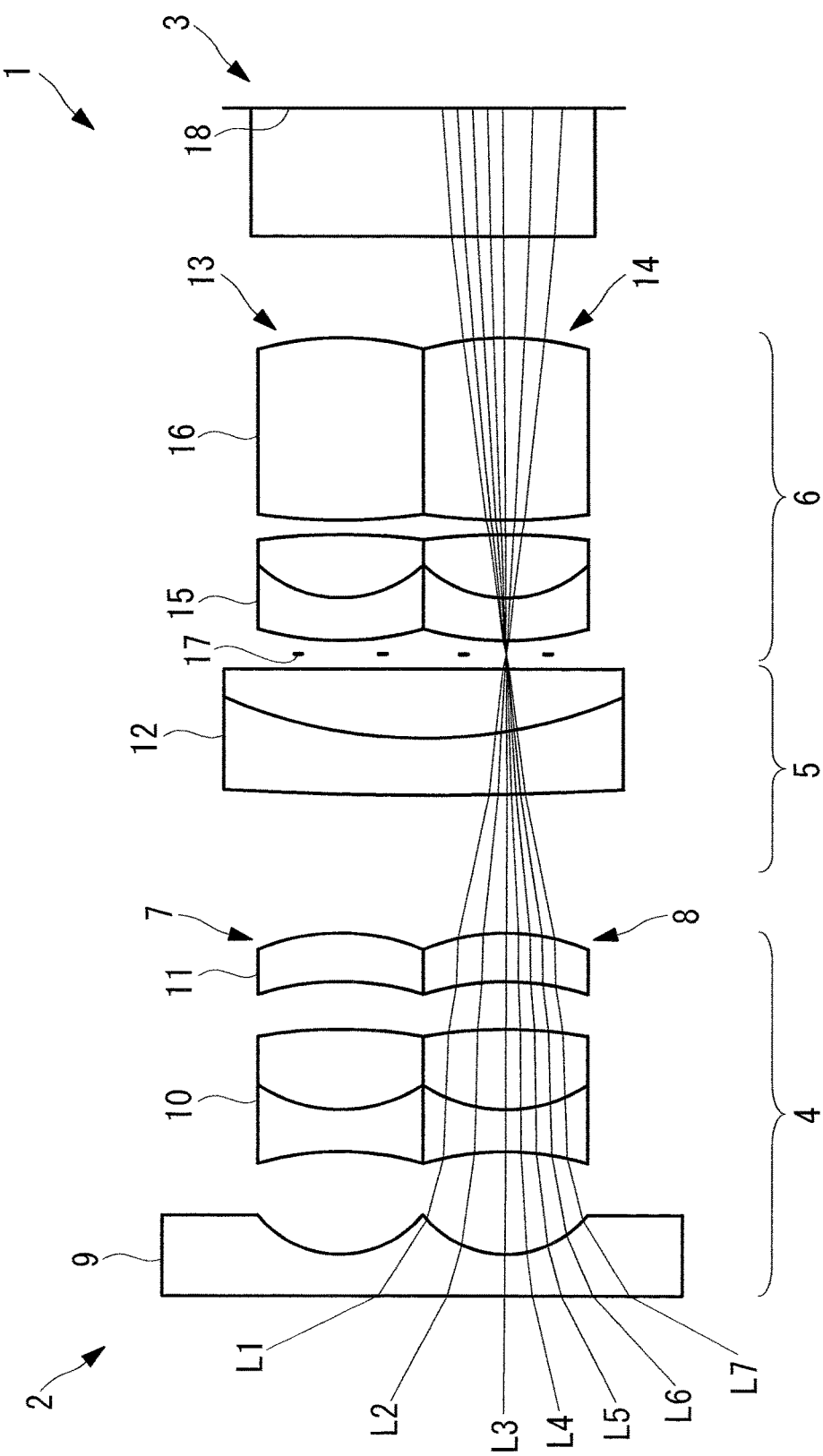
FIG. 2 is a view showing ray tracing of the principal ray when the moving lens in the image acquisition device shown in FIG. 1 is located at a near-point position.

The image acquisition device 1 of this embodiment is, for example, an image acquisition device that is provided at the distal end of an insertion portion of an endoscope and, as shown in FIGS. 1 and 2, is provided with an imaging optical system 2 and an image acquisition element 3.

The imaging optical system 2 is provided with, in order from an object side toward an image side, a first negative lens group 4 having a negative refractive power, a first positive lens group 5 having a positive refractive power, and a second positive lens group 6 having a positive refractive power, and forms two parallax images.

The first negative lens group 4 is provided with two negative lens groups 7 and 8 that are disposed side by side in the parallax direction corresponding to the two parallax images and that have central axes A and B, respectively.

The respective negative lens groups 7 and 8 of the first negative lens group 4 have, in order from the object side, a plano-concave lens 9 that has concave surfaces on the image side thereof, a combined lens 10 that is made up of a biconcave lens and a biconvex lens, and one meniscus lens 11 that has concave surfaces on the object side thereof. Furthermore, as the combined lens 10, lenses of which only two surfaces, i.e., an object-side surface and an image-side surface, are in contact with air on the central axes A and B are lens components.

Figure 3:
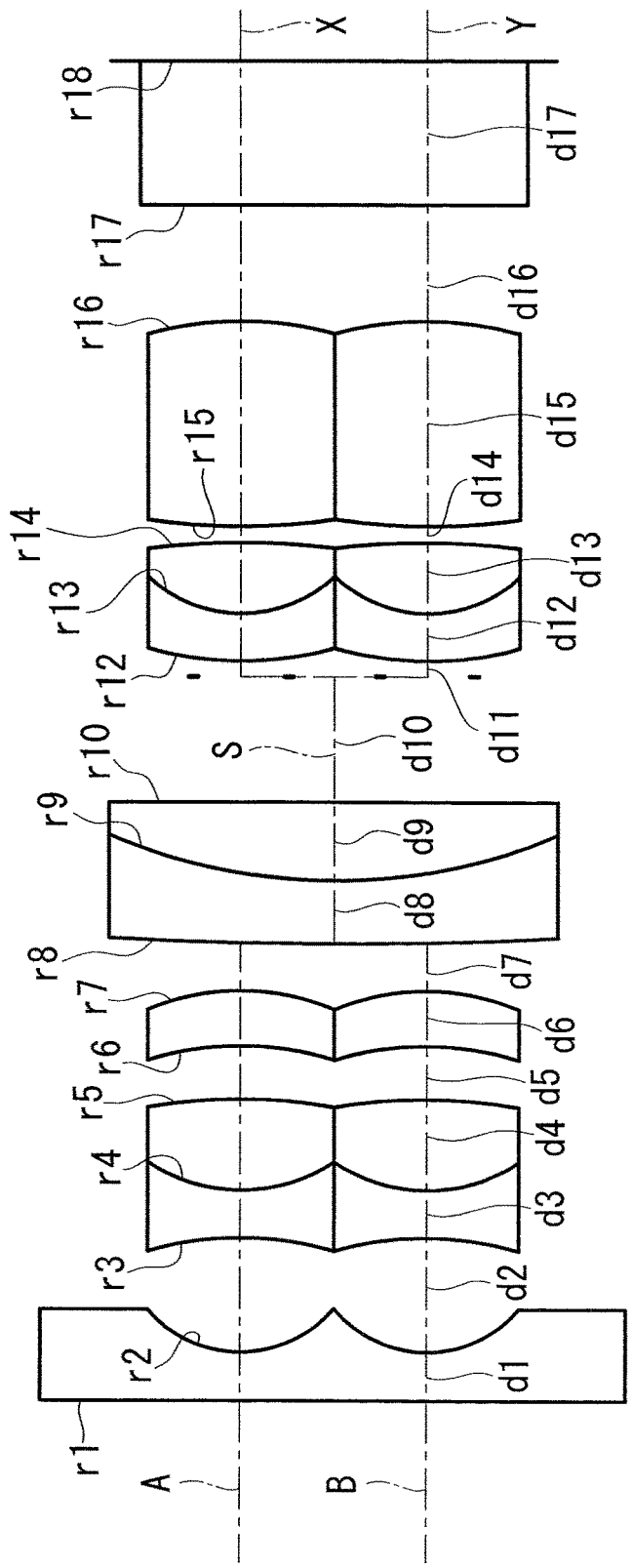
FIG. 3 is a view showing a lens array of an imaging optical system according to Example 1 of the image acquisition device shown in FIG. 1.
Figure 4:
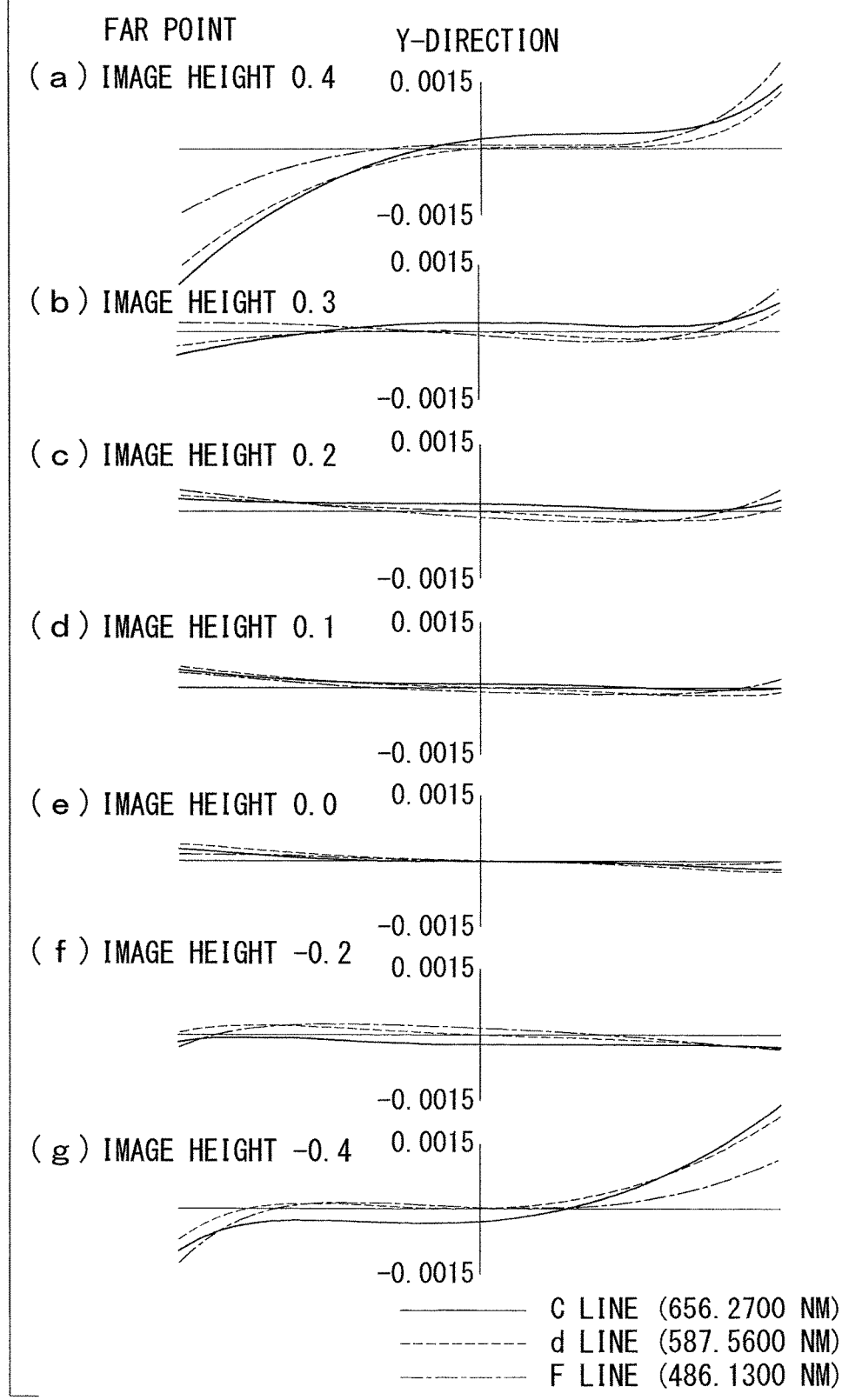
FIG. 4 is a view showing lateral aberrations of (a) a light ray L7, (b) a light ray L6, (c) a light ray L5, (d) a light ray L4, (e) a light ray L3, (f) a light ray L2, and (g) a light ray L1 in the Y-direction when the moving lens group in the imaging optical system shown in FIG. 3 is located at the far-point position shown in FIG. 1.
Figure 5:
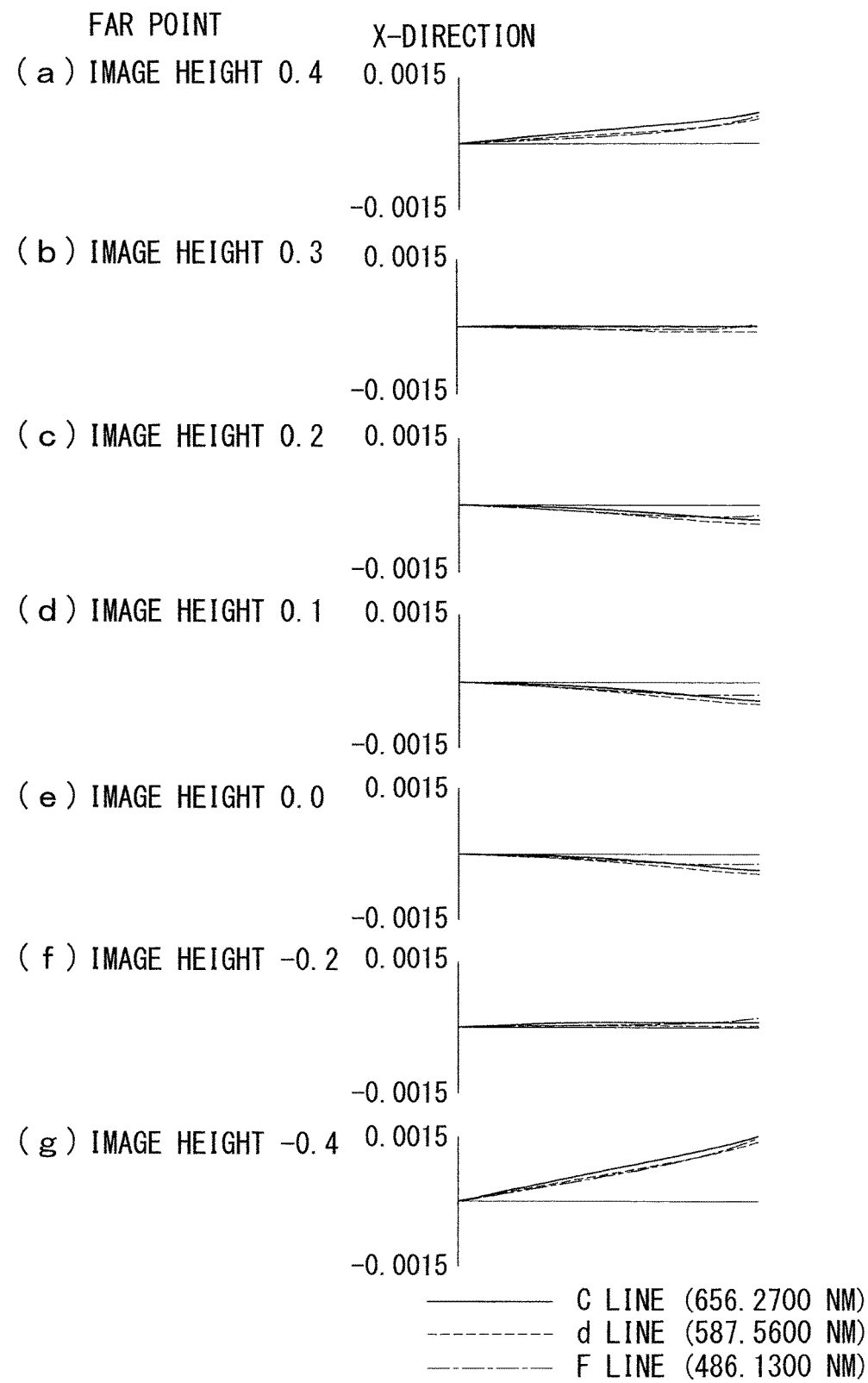
FIG. 5 is a view showing lateral aberrations of (a) the light ray L7, (b) the light ray L6, (c) the light ray L5, (d) the light ray L4, (e) the light ray L3, (f) the light ray L2, and (g) the light ray L1 in the X-direction when the moving lens group in the imaging optical system shown in FIG. 3 is located at the far-point position shown in FIG. 1.
Figure 7:
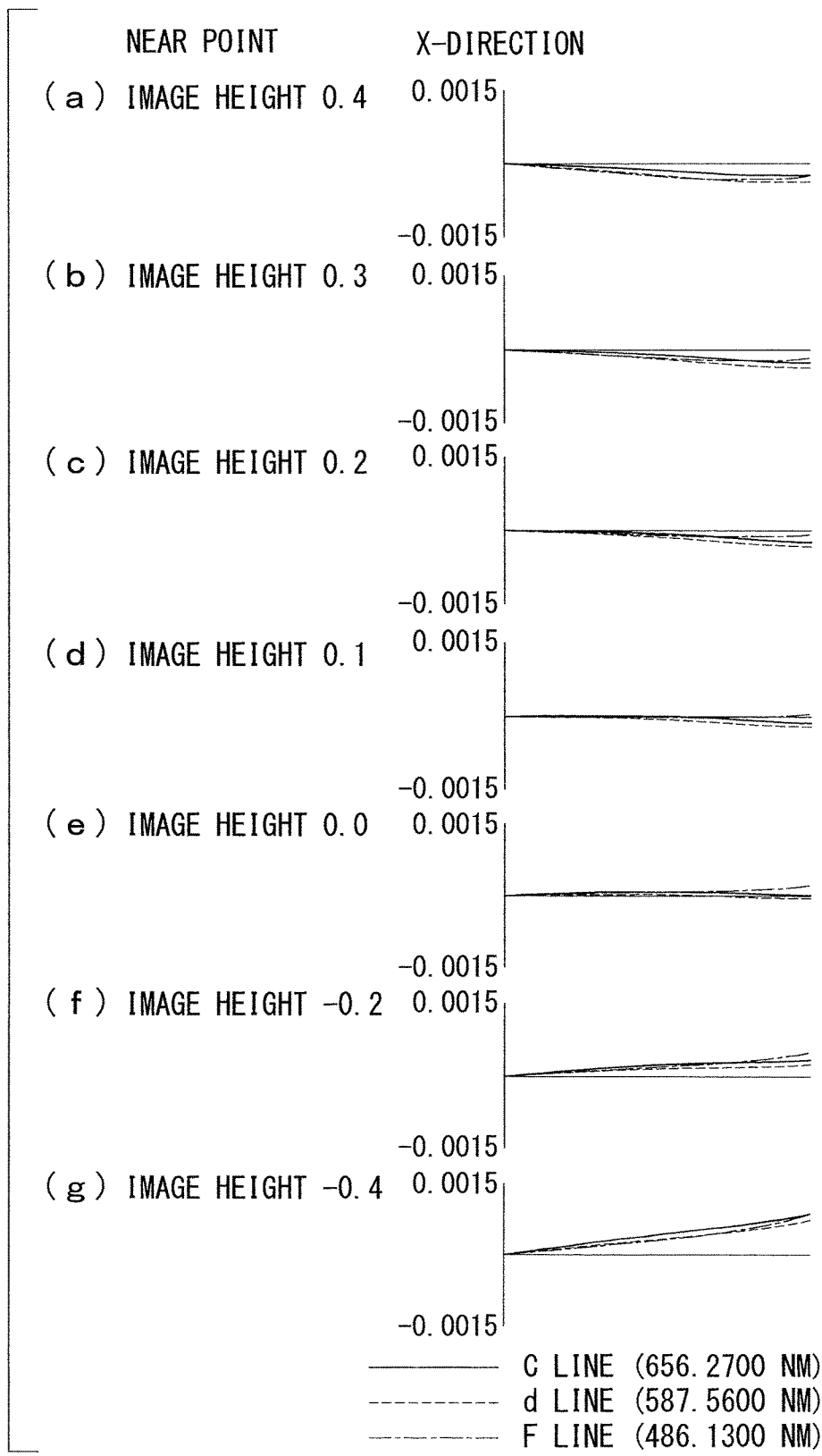
FIG. 7 is a view showing lateral aberrations of (a) the light ray L7, (b) the light ray L6, (c) the light ray L5, (d) the light ray L4, (e) the light ray L3, (f) the light ray L2, and (g) the light ray L1 in the X-direction when the moving lens group in the imaging optical system shown in FIG. 3 is located at the near-point position shown in FIG. 2.

As shown in FIG. 3, the first positive lens group 5 has a single central axis (common central axis) S, is a common lens group that causes light rays emitted from the respective negative lens groups 7 and 8 in the first negative lens group 4 to pass therethrough, and is formed of a combined lens 12 made up of a meniscus lens having a convex surface on the object side thereof and a biconvex lens. The first positive lens group 5 forms a moving lens group that is provided movably along the common central axis S.

The second positive lens group 6 is provided with two positive lens groups 13 and 14 that are disposed side by side in the parallax direction corresponding to the parallax images and that have central axes X and Y, respectively.

The respective positive lens groups 13 and 14 in the second positive lens group 6 have, in order from the object side, a combined lens 15 that is made up of a meniscus lens having a convex surface on the object side thereof and a biconvex lens, and a biconvex lens 16. An aperture stop (stop) 17 that has openings corresponding to the parallax images is provided between the first positive lens group 5 and the second positive lens group 6.

Light rays from an object are collected, in a state in which they are separated into two according to the parallax, by the two negative lens groups 7 and 8 in the first negative lens group 4, pass through the first positive lens group 5, which is the common lens group, and, when entering the second positive lens group 6, are again separated into two according to the parallax, thereby being formed into two parallax images by means of the respective positive lens groups 13 and 14, which constitute the second positive lens group 6.

The image acquisition element 3 is formed of a CCD, a CMOS, or the like in which an imaging surface 18 is disposed at imaging positions of the parallax images formed by the second positive lens group 6.

The image acquisition device 1 of this embodiment satisfies the following conditions (1) to (4).

$$fm > (Dk \times \Delta D)/(ih \times 0.2) \quad (1)$$

$$-1.6 < fGN1/fGP2 < -0.6 \quad (2)$$

$$-1.5 < Dk/fGN1 < 0 \quad (3)$$

$$1 > Dk/fGP2 > 0 \quad (4)$$

Here, fm indicates the absolute value of the focal length of the moving lens group 5, ΔD indicates the maximum amount of movement of the moving lens group 5, ih indicates the image height of a parallax image, Dk indicates the distance between the central axes X and Y of the two positive lens groups 13 and 14, which constitute the second positive lens group 6, fGN1 indicates the focal length of the first negative lens group 4, and fGP2 indicates the focal length of the second positive lens group 6.

The amount of change ΔY in the image height caused by the maximum amount of movement ΔD of the combined lens 12 satisfies the following relational expression.

$$\Delta Y = \Delta D \times (Dk/2)/fm$$

Then, condition (1) is derived, provided that the amount of change ΔY in the image height is smaller than 10% of the image height ih, specifically, $$\Delta Y < ih \times 0.1.$$

The operation of the thus-configured image acquisition device 1 of this embodiment will be described below.

According to the image acquisition device 1 of this embodiment, when light rays from an object enter the image acquisition device 1, two images having parallax are formed in the imaging optical system 2, and the two parallax images are acquired by the image acquisition element 3. The light rays from the object are separated into two according to parallax and are collected by the two negative lens groups 7 and 8, which constitute the first negative lens group 4, thus making it possible to secure a wide angle of view and causing the diameters of light fluxes collected by the first negative lens group 4 to be kept narrow by the first positive lens group 5, which is provided at the sequent stage. Then, the light rays passing through the first positive lens group 5 enter the second positive lens group 6, which is provided with the two positive lens groups 13 and 14 disposed side by side in the parallax direction, thereby being separated again into two parallax images, and the two parallax images are acquired by the image acquisition element 3.

To adjust the focus position, the single combined lens 12, which forms the first positive lens group 5, is moved along the common central axis S, thus making it possible to adjust the focus position with a simple movement mechanism.

Accordingly, it is possible to achieve a reduction in the diameter and a reduction in the length of the image acquisition device 1. Specifically, according to the image acquisition device 1 of this embodiment, there is an advantage in that the structure is simplified, thus making it possible to prevent an increase in size and to sufficiently increase the angle of view.

Furthermore, in this case, because the first positive lens group 5, which is disposed between the first negative lens group 4 and the second positive lens group 6 and which is the common lens group, is moved along the common central axis S, the second positive lens group 6, which is close to the image acquisition element 3, need not be moved. Thus, there is an advantage in that it is possible to reduce the distance between the central axes X and Y of the two positive lens groups 13 and 14 in the second positive lens group 6 and to minimize the parallax.

Furthermore, it is possible to reduce the impact of a driving error when the first positive lens group 5 is moved along the common central axis S, compared with a case in which the second positive lens group 6 is moved. Furthermore, there is an advantage in that the incident angles at the image acquisition element 3 are minimized, thus making it possible to prevent a reduction in detection sensitivity caused by oblique incidence.

Furthermore, because the first positive lens group 5 is formed of the combined lens 12, which is made up of the meniscus lens having a convex surface on the image side thereof and the biconvex lens, it is possible to suppress a fluctuation of chromatic aberration caused by movement thereof.

Note that the aperture stop 17 may be eccentrically disposed with respect to the each of the central axes X and Y of the two positive lens groups 13 and 14 in the second positive lens group 6. By doing so, there is an advantage in that, even when the entrance pupil positions are close together, the imaging positions of the parallax images can be shifted, thus making it possible to reduce vignetting of the light fluxes.

Furthermore, the distance between the centers of the two openings of the aperture stop 17 may be larger than the distance between the central axes X and Y of the two positive lens groups 13 and 14 in the second positive lens group 6. By doing so, it is possible to reduce crosstalk of the parallax images obtained when the imaging angle of view is increased.

Furthermore, the distance between the centers of the two openings of the aperture stop 17 may be smaller than the distance between the central axes X and Y of the two positive lens groups 13 and 14 in the second positive lens group 6. By doing so, the distance between the parallax images is reduced, thus making it possible to reduce the size of the imaging surface 18 of the image acquisition element 3.

Furthermore, in the image acquisition device 1 of this embodiment, because condition (1) is satisfied, there is an advantage in that it is possible to suppress an aberration caused by a driving error of the moving lens group 5.

Furthermore, in the image acquisition device 1 of this embodiment, because condition (2) is satisfied, it is possible to reduce a fluctuation in aberration when the moving lens group 5 is moved.

Furthermore, in the image acquisition device 1 of this embodiment, conditions (3) and (4) are satisfied, there is an advantage in that aberration can be reduced.

Next, Example 1 of the image acquisition device 1 of this embodiment will be described below by using FIGS. 3 to 7 and lens data.

FIG. 3 shows a lens array of the imaging optical system 2 of the image acquisition device 1 of this Example. Furthermore, FIGS. 4 to 7 are aberration diagrams corresponding to respective light rays L1 to L7 in the imaging optical system 2 of this Example.

In this Example, the maximum angle of view (far point) is 120', the image height is 0.4 mm, and the Fno is 4.

In the following lens data, r indicates the radius of curvature (mm), d indicates inter-surface distance (mm), Nd indicates the refractive index with respect to the d line, and ν indicates the Abbe number. Furthermore, OBJ indicates a subject (object).

| surface number | r | d | Nd | ν |
|---|---|---|---|---|
| OBJ | ∞ | 16 | | |
| 1 | ∞ | 0.3 | 1.74397 | 44.8496 |
| 2 | 0.682985 | 0.728907 | | |
| 3 | −1.81916 | 0.3 | 1.744 | 44.7857 |
| 4 | 0.96296 | 0.564563 | 1.74179 | 28.1424 |
| 5 | −3.04455 | 0.337757 | | |
| 6 | −1.77654 | 0.35 | 1.58913 | 61.1341 |
| 7 | −1.33214 | 0.3 | | |
| 8 | 24.5511 | 0.4 | 1.7552 | 27.5116 |
| 9 | 3.19977 | 0.5 | 1.72568 | 30.5685 |
| 10 | −572.442 | 0.77725 | | |
| 11 | ∞ (stop) | 0.1 | | |
| 12 | 1.90494 | 0.3 | 1.75512 | 27.6565 |
| 13 | 0.766695 | 0.448757 | 1.58913 | 61.1341 |
| 14 | −3.9825 | 0.1 | | |
| 15 | 3.85409 | 1.28188 | 1.48749 | 70.2353 |
| 16 | −1.90788 | 0.715974 | | |
| 17 | ∞ | 0.9 | 1.51633 | 64.1411 |
| 18 | ∞ (imaging surface) | | | |

The object point, the inter-surface distance 7, and the inter-surface distance 10 in the above-described lens data show values obtained when the moving lens group 5 is located at a far-point position. Values obtained when the moving lens group 5 is located at a near-point position are: dOBJ (the distance from the object to the first surface)=6 mm; d7=0.97725 mm; and d10=0.1 mm.

Furthermore, the eleventh surface denotes the aperture stop 17, and the amounts of eccentricities yde at the eighth surface, the eleventh surface, and the eighteenth surface with respect to the central axis S at the object sides thereof are:
eighth surface: yde=0.55 mm;
eleventh surface: yde=−0.55 mm; and
eighteenth surface: yde=0.02 mm, respectively.

Next, Example 2 of the image acquisition device 1 of this embodiment will be described below by using FIGS. 8 to 12 and lens data.

Figure 8:
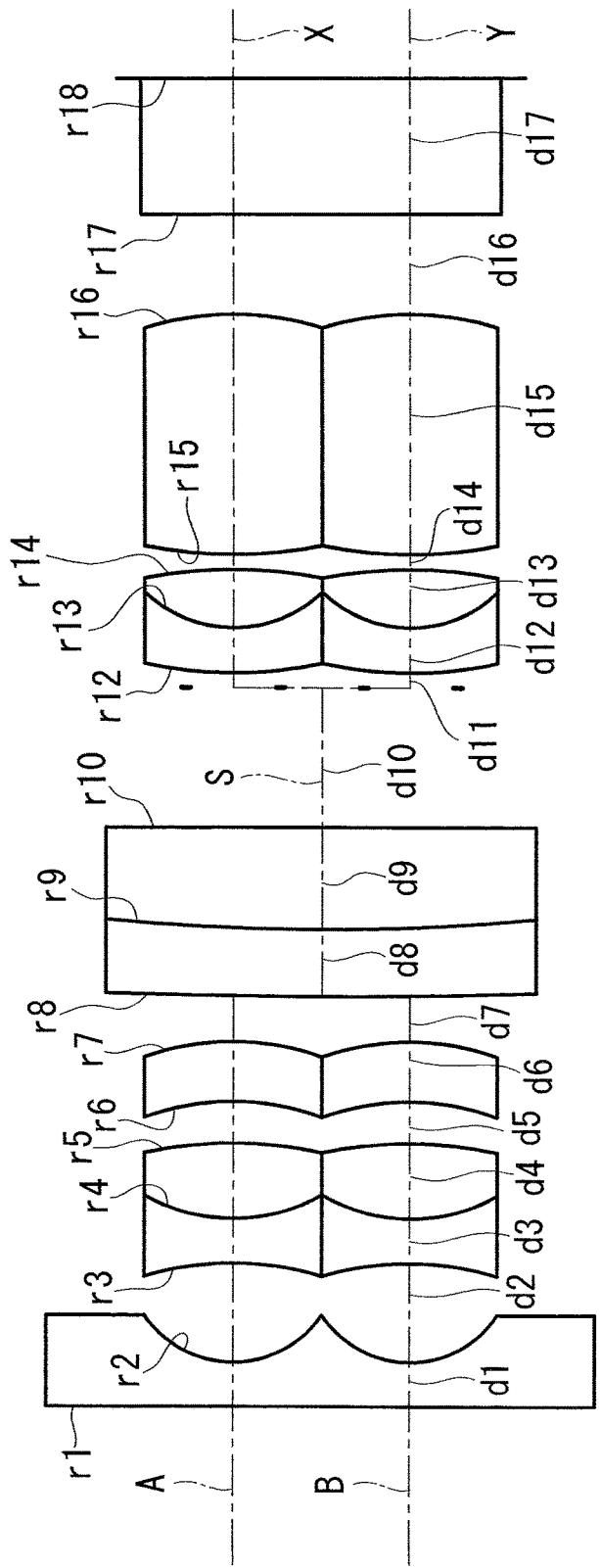
FIG. 8 is a view showing a lens array of an imaging optical system according to Example 2 of the image acquisition device shown in FIG. 1.
Figure 9:
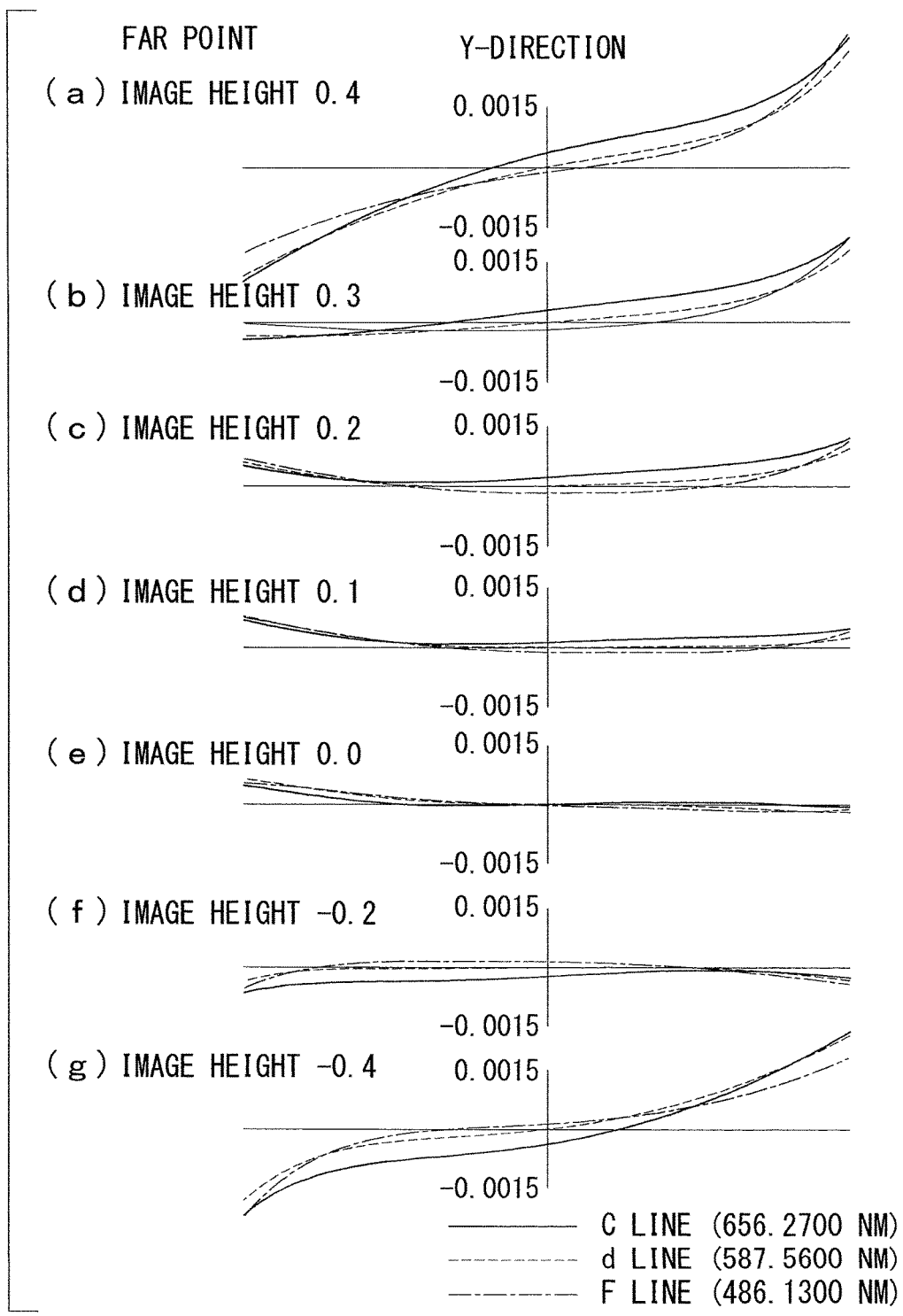
FIG. 9 is a view showing lateral aberrations of (a) the light ray L7, (b) the light ray L6, (c) the light ray L5, (d) the light ray L4, (e) the light ray L3, (f) the light ray L2, and (g) the light ray L1 in the Y-direction when the moving lens group in the imaging optical system shown in FIG. 8 is located at the far-point position.
Figure 10:
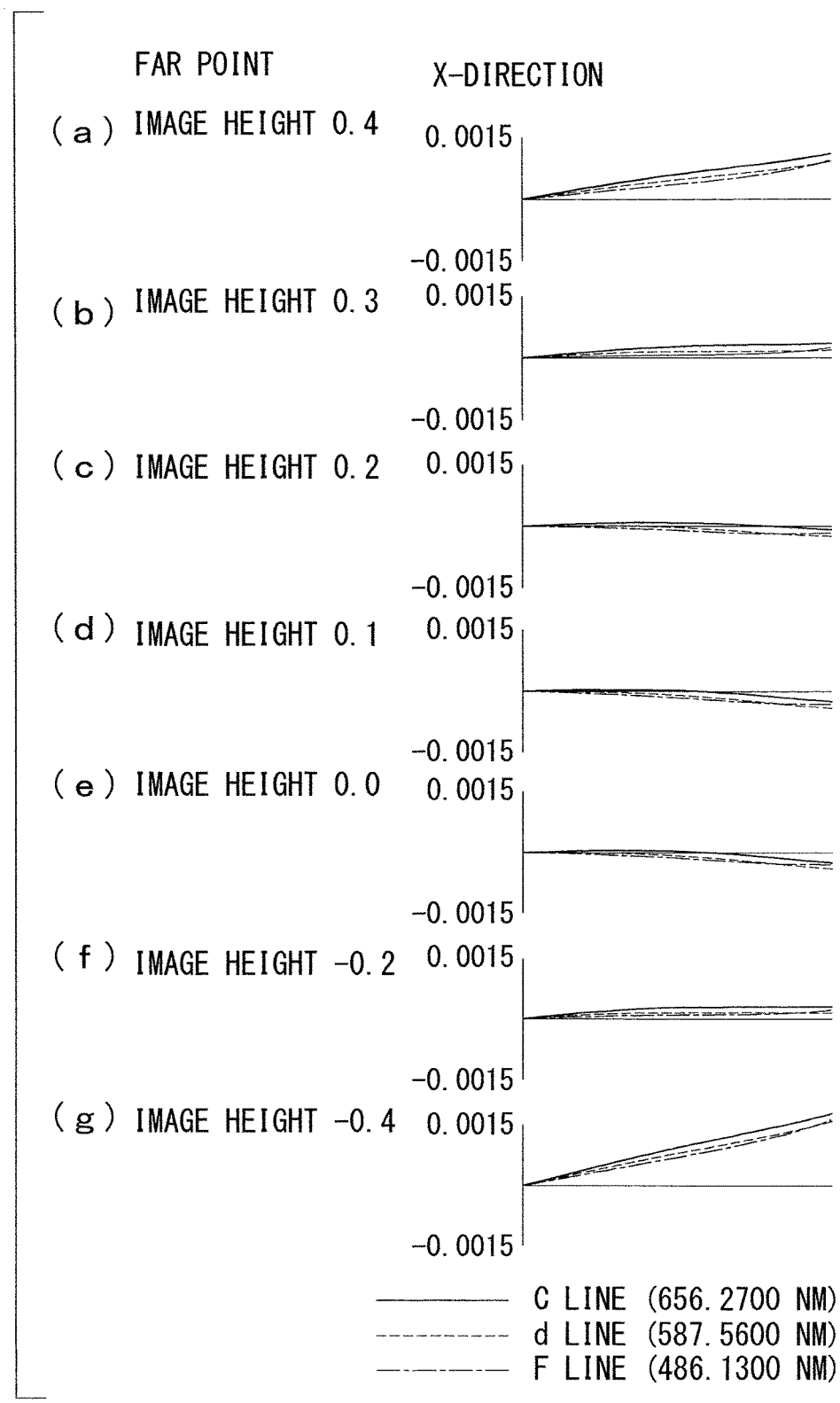
FIG. 10 is a view showing lateral aberrations of (a) the light ray L7, (b) the light ray L6, (c) the light ray L5, (d) the light ray L4, (e) the light ray L3, (f) the light ray L2, and (g) the light ray L1 in the X-direction when the moving lens group in the imaging optical system shown in FIG. 8 is located at the far-point position.
Figure 11:
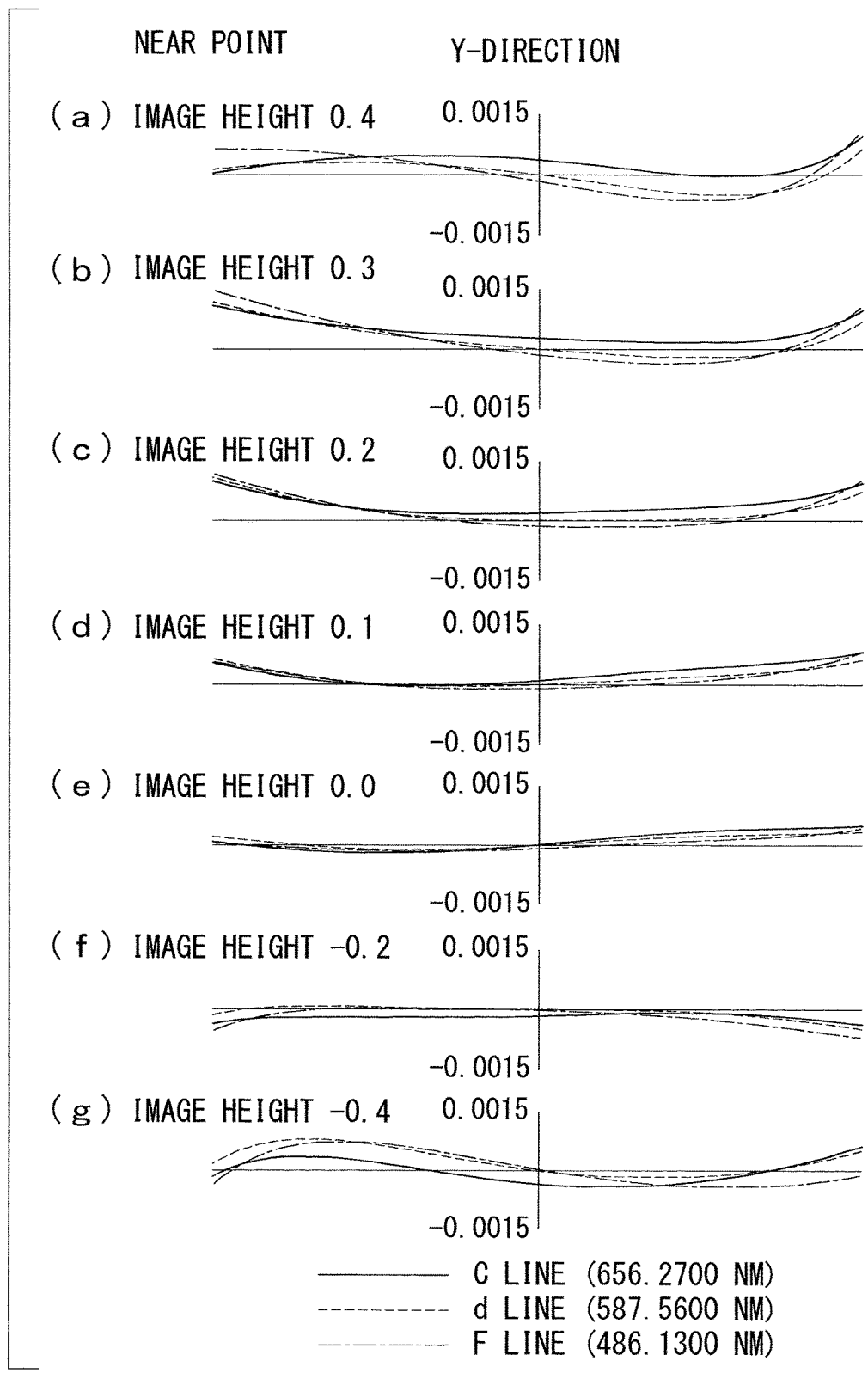
FIG. 11 is a view showing lateral aberrations of (a) the light ray L7, (b) the light ray L6, (c) the light ray L5, (d) the light ray L4, (e) the light ray L3, (f) the light ray L2, and (g) the light ray L1 in the Y-direction when the moving lens group in the imaging optical system shown in FIG. 8 is located at the near-point position.
Figure 12:
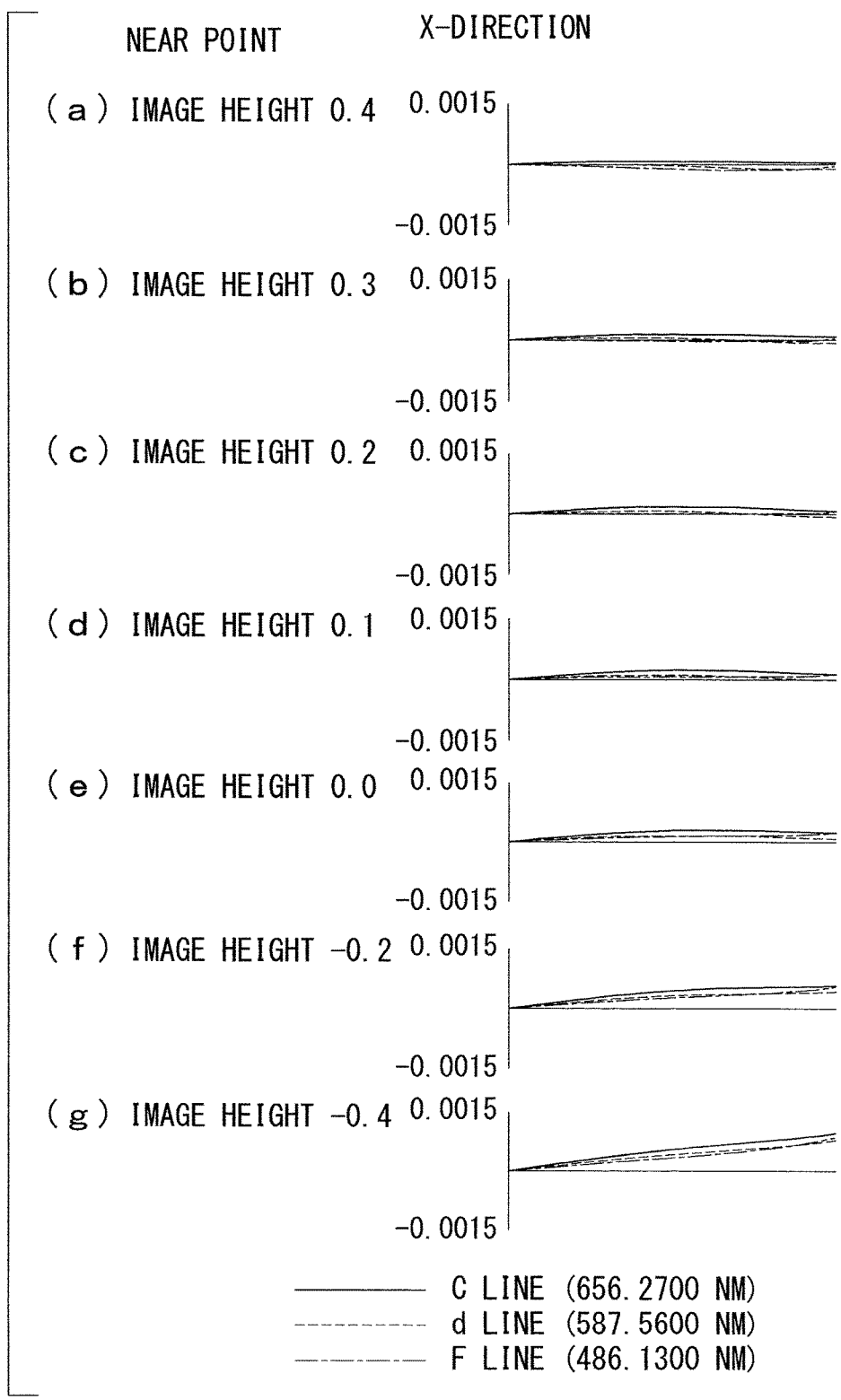
FIG. 12 is a view showing lateral aberrations of (a) the light ray L7, (b) the light ray L6, (c) the light ray L5, (d) the light ray L4, (e) the light ray L3, (f) the light ray L2, and (g) the light ray L1 in the X-direction when the moving lens group in the imaging optical system shown in FIG. 8 is located at the near-point position.

FIG. 8 shows a lens array of the imaging optical system 2 of the image acquisition device 1 of this Example. Furthermore, FIGS. 9 to 12 are aberration diagrams corresponding to respective light rays L1 to L7 in the imaging optical system 2 of this Example.

In this Example, the maximum angle of view (far point) is 122°, the image height is 0.4 mm, and the Fno is 3.5.

| surface number | r | d | Nd | ν |
|---|---|---|---|---|
| OBJ | ∞ | 18 | | |
| 1 | ∞ | 0.3 | 1.74397 | 44.8496 |

-continued

| surface number | r | d | Nd | ν |
|---|---|---|---|---|
| 2 | 0.75403 | 0.667151 | | |
| 3 | −1.94 | 0.3 | 1.74397 | 44.8496 |
| 4 | 1.24367 | 0.502807 | 1.7552 | 27.5116 |
| 5 | −3.40025 | 0.276001 | | |
| 6 | −1.81523 | 0.4 | 1.74077 | 27.7889 |
| 7 | −1.61417 | 0.3 | | |
| 8 | 46.134 | 0.45 | 1.7552 | 27.579 |
| 9 | 15.8259 | 0.7 | 1.744 | 44.7857 |
| 10 | −350.734 | 0.908629 | | |
| 11 | ∞ (stop) | 0.1 | | |
| 12 | 2.49423 | 0.3 | 1.7552 | 27.5116 |
| 13 | 0.901324 | 0.387 | 1.58913 | 61.1341 |
| 14 | −2.83366 | 0.1 | | |
| 15 | 3.27814 | 1.58694 | 1.54498 | 65.0511 |
| 16 | −2.22465 | 0.654218 | | |
| 17 | ∞ | 0.9 | 1.51633 | 64.1411 |
| 18 | ∞ (imaging surface) | | | |

The object point, the inter-surface distance 7, and the inter-surface distance 10 in the above-described lens data show values obtained when the moving lens group 5 is located at the far-point position. Values obtained when the moving lens group 5 is located at the near-point position are: dOBJ (the distance from the object to the first surface)=6 mm; d7=1.10863 mm; and d10=0.1 mm.

Furthermore, the eleventh surface denotes the aperture stop 17, and the amounts of eccentricities yde at the eighth surface, the eleventh surface, and the eighteenth surface with respect to the central axis S at the object sides thereof are:
eighth surface: yde=0.6 mm;
eleventh surface: yde=−0.6 mm; and
eighteenth surface: yde=0.014012 mm, respectively.

Next, an image acquisition device 20 according to a second embodiment of the present invention will be described below with reference to the drawings.

In the explanation of this embodiment, identical reference signs are assigned to portions having configurations common to those in the image acquisition device 1 of the above-described first embodiment, and a description thereof will be omitted.

Figure 13:
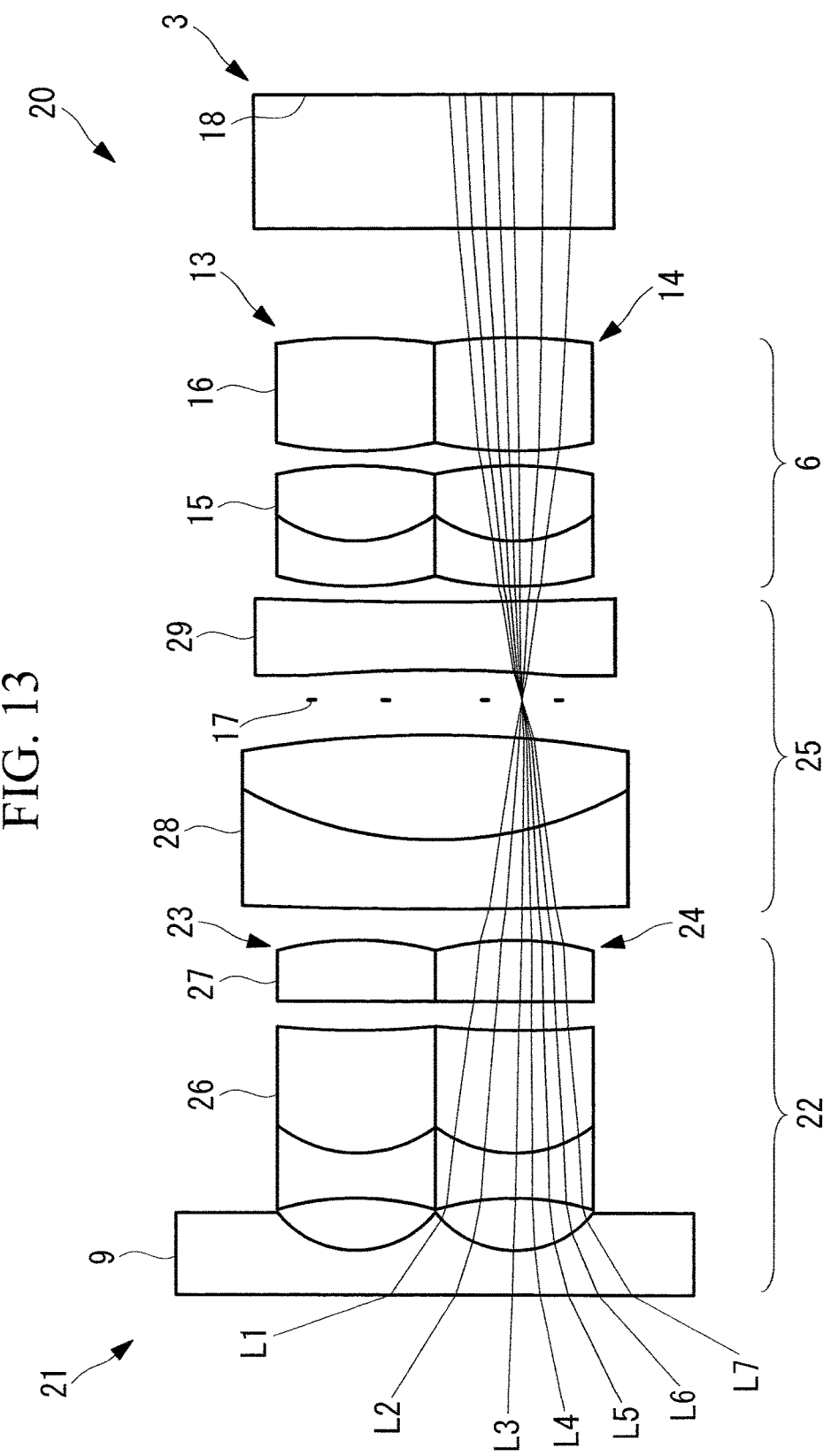
FIG. 13 is a view showing ray tracing of the principal ray when a moving lens group in an image acquisition device according to a second embodiment of the present invention is located at the far-point position.
Figure 14:
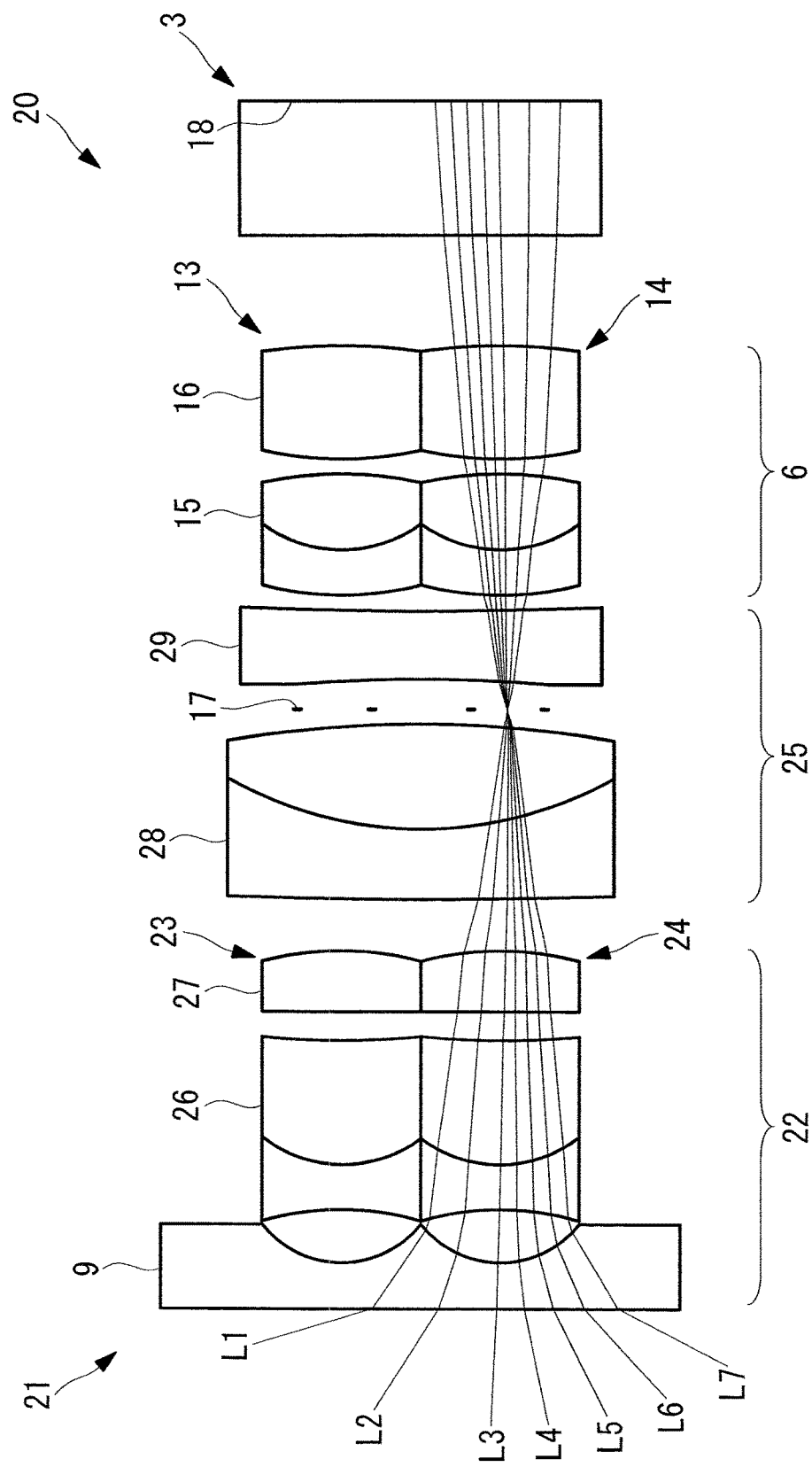
FIG. 14 is a view showing ray tracing of the principal ray when the moving lens in the image acquisition device shown in FIG. 13 is located at the near-point position.

As shown in FIGS. 13 and 14, this embodiment differs from the image acquisition device 1 of the first embodiment in terms of two negative lens groups 23 and 24 in a first negative lens group 22, and a first positive lens group 25.

This embodiment differs from the image acquisition device 1 of the first embodiment in that the two negative lens groups 23 and 24 in the first negative lens group 22 include: a combined lens 26 that is made up of a biconcave lens and a meniscus lens having a concave surface on the image side thereof; and a biconvex lens 27.

Furthermore, this embodiment differs from the image acquisition device 1 of the first embodiment in that the first positive lens group 25 is provided with, in order from the object side: a combined lens 28 that is made up of a meniscus lens having a convex surface on the object side thereof and a biconvex lens; and one biconcave lens 29, and in that the combined lens 28 forms a moving lens group.

Furthermore, this embodiment differs from the image acquisition device 1 of the first embodiment in that the aperture stop 17 having openings corresponding to respective parallax images is provided between the combined lens 28 and the biconcave lens 29, which constitute the first positive lens group 25.

According to the image acquisition device 20 of this embodiment, because the first positive lens group 25 is provided with the plurality of lens groups, which are disposed with a space which is variable, and the plurality of lens groups include the combined lens (positive lens group) 28, which has a positive refractive power, and the biconcave lens (negative lens group) 29, which has a negative refractive power, there is an advantage in that a shift of the optical axis in the common lens can be suppressed by means of a combination of concavity and convexity.

Furthermore, according to the image acquisition device 20 of this embodiment, because the aperture stop 17, which has the openings corresponding to the respective parallax, is provided between the combined lens 28 and the biconcave lens 29, it is possible to minimize the spreading of the light fluxes at the position of the aperture stop 17 and to suppress the spreading of the light fluxes at the image side and the object side of the aperture stop 17. Accordingly, it is possible to suppress both the effective diameter of the first negative lens group 22 and the effective diameter of the second positive lens group 6 and to reduce the impact of vignetting. Then, even when the distance between the pupils of the negative lens groups 23 and 24 in the first negative lens group 22 is not increased, it is possible to acquire parallax images with a wide angle of view and to achieve a reduction in size.

Next, Example 3 of the image acquisition device 20 of this embodiment will be described below by using FIGS. 15 to 19 and lens data.

Figure 15:
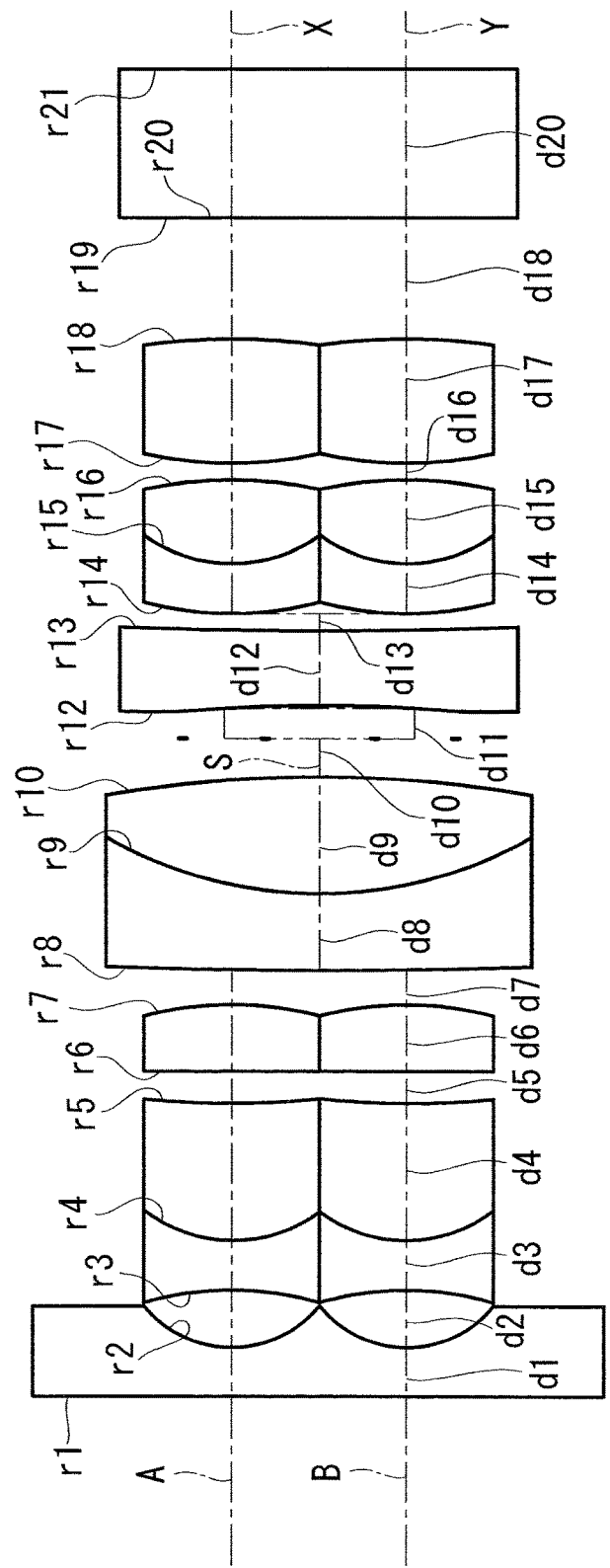
FIG. 15 is a view showing a lens array of an imaging optical system according to Example 3 of the image acquisition device shown in FIG. 13.
Figure 16:
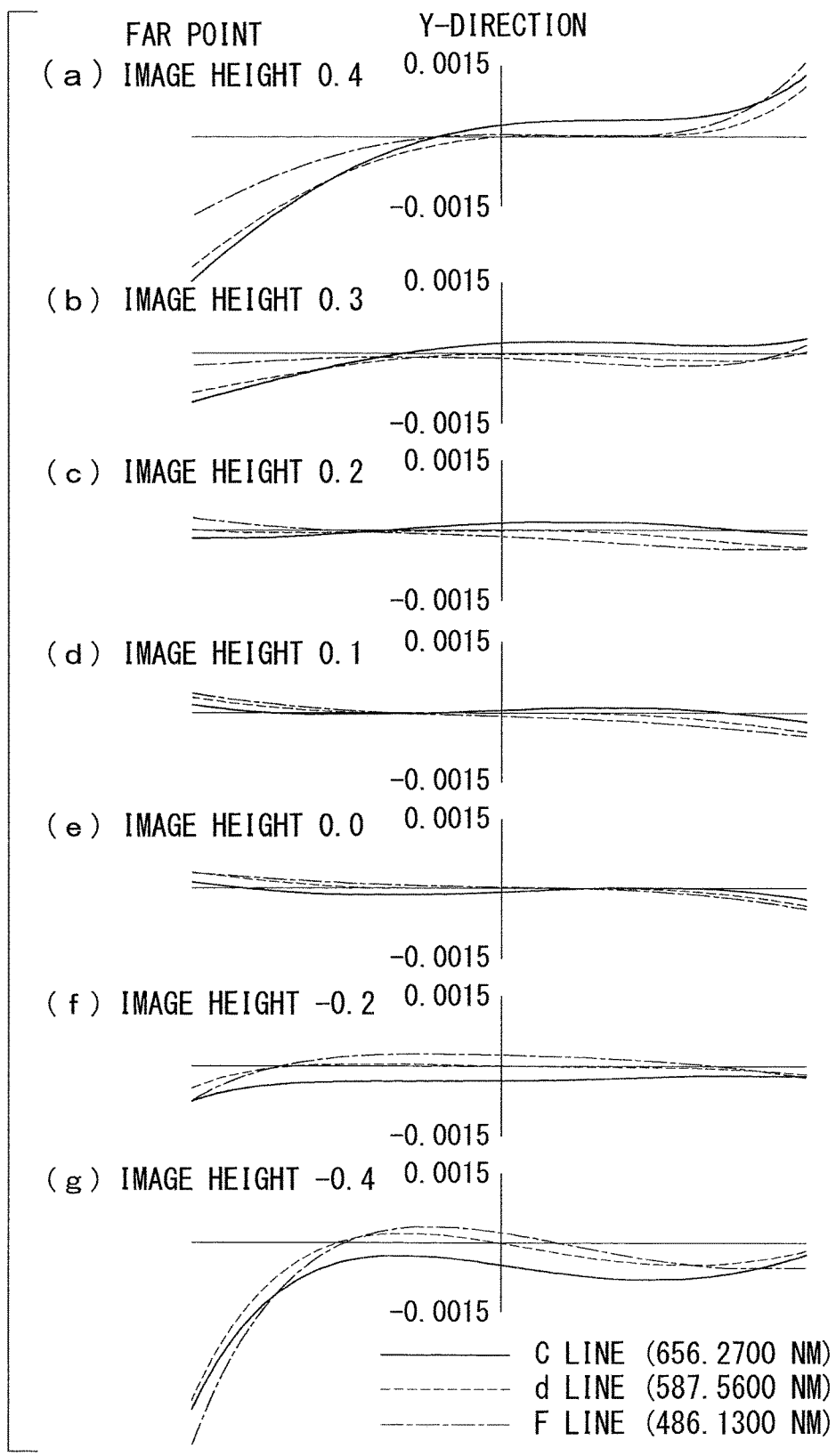
FIG. 16 is a view showing lateral aberrations of (a) the light ray L7, (b) the light ray L6, (c) the light ray L5, (d) the light ray L4, (e) the light ray L3, (f) the light ray L2, and (g) the light ray L1 in the Y-direction when the moving lens group in the imaging optical system shown in FIG. 15 is located at the far-point position shown in FIG. 13.
Figure 18:
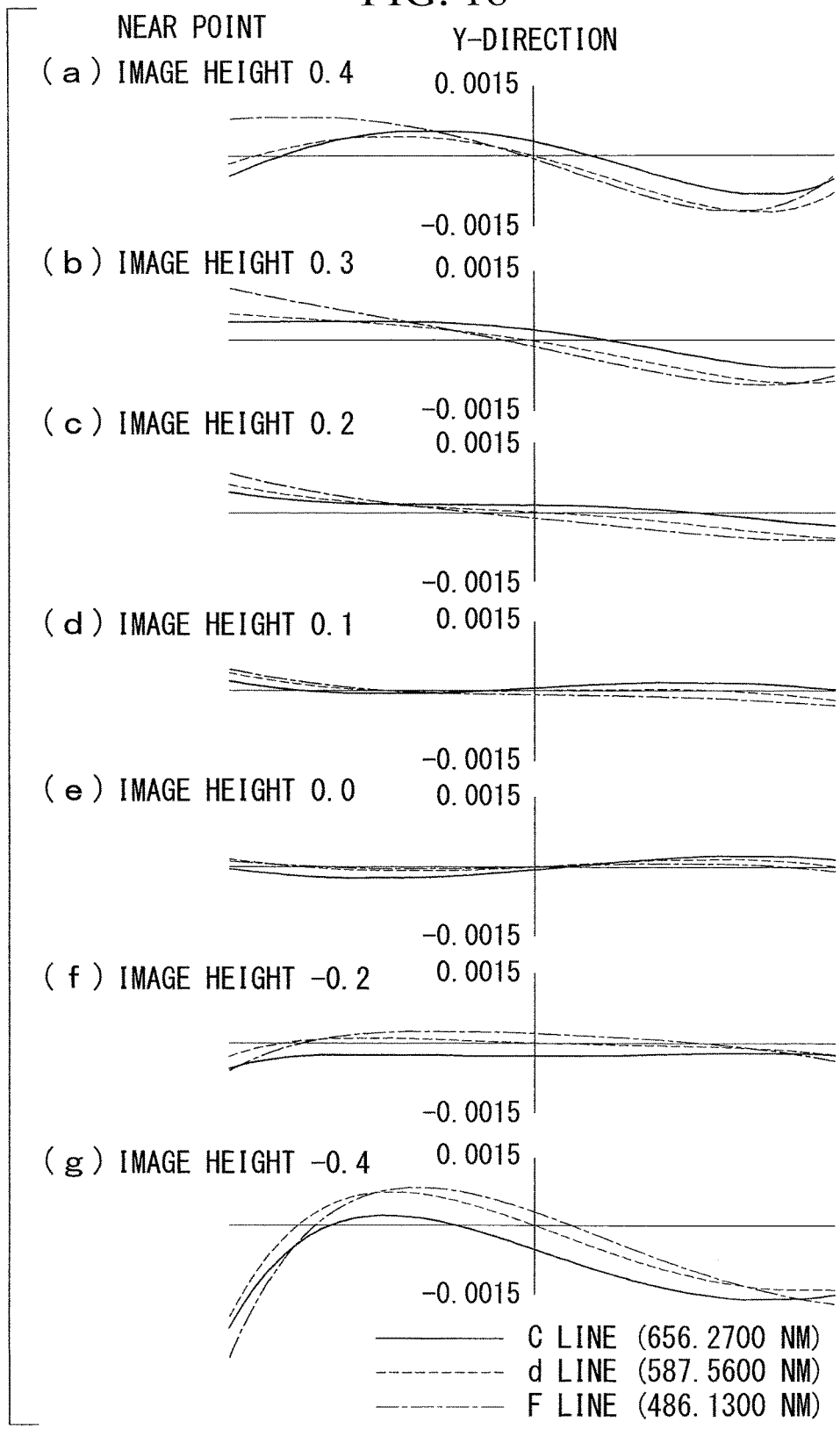
FIG. 18 is a view showing lateral aberrations of (a) the light ray L7, (b) the light ray L6, (c) the light ray L5, (d) the light ray L4, (e) the light ray L3, (f) the light ray L2, and (g) the light ray L1 in the Y-direction when the moving lens group in the imaging optical system shown in FIG. 15 is located at the near-point position shown in FIG. 14.
Figure 19:
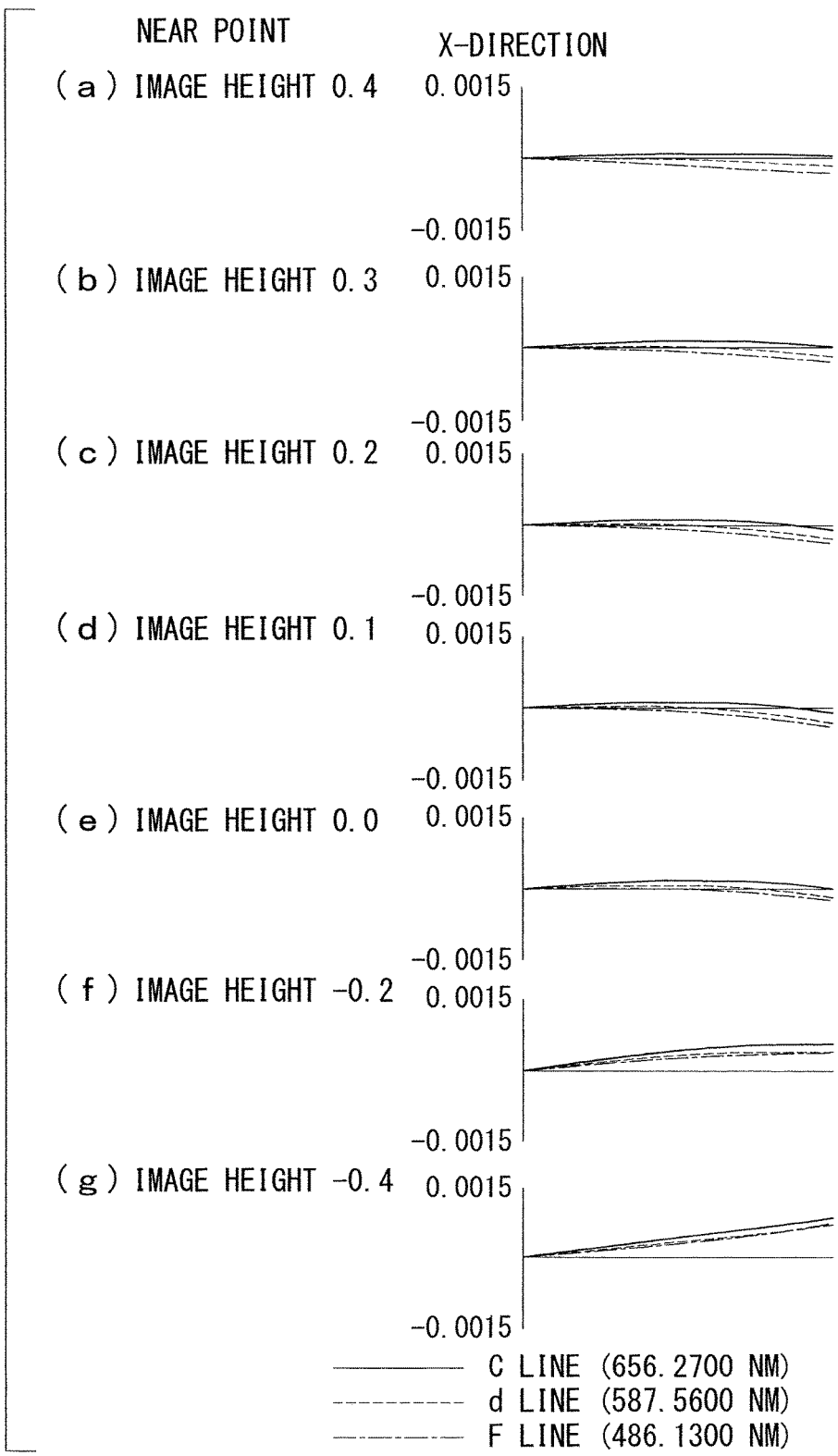
FIG. 19 is a view showing lateral aberrations of (a) the light ray L7, (b) the light ray L6, (c) the light ray L5, (d) the light ray L4, (e) the light ray L3, (f) the light ray L2, and (g) the light ray L1 in the X-direction when the moving lens group in the imaging optical system shown in FIG. 15 is located at the near-point position shown in FIG. 14.

FIG. 15 shows a lens array of an imaging optical system 21 of the image acquisition device 20 of this Example. Furthermore, FIGS. 16 to 19 are aberration diagrams corresponding to respective light rays L1 to L7 in the imaging optical system 21 of this Example.

In this Example, the maximum angle of view (far point) is 140°, the image height is 0.4 mm, and the Fno is 4.

| surface number | r | d | Nd | ν |
|---|---|---|---|---|
| OBJ | ∞ | 16 | | |
| 1 | ∞ | 0.3 | 1.74341 | 44.893 |
| 2 | 0.624603 | 0.35 | | |
| 3 | −1.83849 | 0.3 | 1.65011 | 55.095 |
| 4 | 0.8 | 0.824461 | 1.7552 | 27.5116 |
| 5 | 3.19726 | 0.2 | | |
| 6 | 41.729 | 0.4 | 1.61717 | 52.3378 |
| 7 | −1.68972 | 0.224506 | | |
| 8 | 55.6494 | 0.45 | 1.74077 | 27.7889 |
| 9 | 2.38544 | 0.7 | 1.73323 | 30.7671 |
| 10 | −6.58301 | 0.231451 | | |
| 11 | ∞ (stop) | 0.2 | | |
| 12 | −12.5835 | 0.45 | 1.6799 | 31.4352 |
| 13 | 17.4312 | 0.1 | | |
| 14 | 1.97593 | 0.3 | 1.7552 | 27.579 |
| 15 | 0.847122 | 0.5 | 1.58913 | 61.1341 |
| 16 | −2.77896 | 0.1 | | |
| 17 | 2.58729 | 0.749325 | 1.62001 | 60.343 |
| 18 | −4.8269 | 0.721822 | | |
| 19 | ∞ (virtual plane) | 0 | | |
| 20 | ∞ | 0.9 | 1.51633 | 64.1411 |
| 21 | ∞ (imaging surface) | | | |

The object point, the inter-surface distance 7, and the inter-surface distance 10 in the above-described lens data show values obtained when the moving lens group 28 is located at the far-point position. Values obtained when the moving lens group 28 is located at the near-point position are: dOBJ (the distance from the object to the first surface)=6 mm; d7=0.355957 mm; and d10=0.1 mm.

Furthermore, the eleventh surface denotes the aperture stop 17, and the amounts of eccentricities yde at the eighth surface, the eleventh surface, the twelfth surface, the fourteenth surface, and the twenty-first surface with respect to the central axis S at the object sides thereof are:
eighth surface: yde=0.5 mm;
eleventh surface: yde=−0.45 mm;
twelfth surface: yde=0.45 mm;
fourteenth surface: yde=−0.5 mm; and
twenty-first surface: yde=0.00266 mm, respectively.

Next, an image acquisition device 30 according to a third embodiment of the present invention will be described below with reference to the drawings.

In the explanation of this embodiment, identical reference signs are assigned to portions having configurations common to those in the image acquisition device 20 of the above-described second embodiment, and a description thereof will be omitted.

Figure 20:
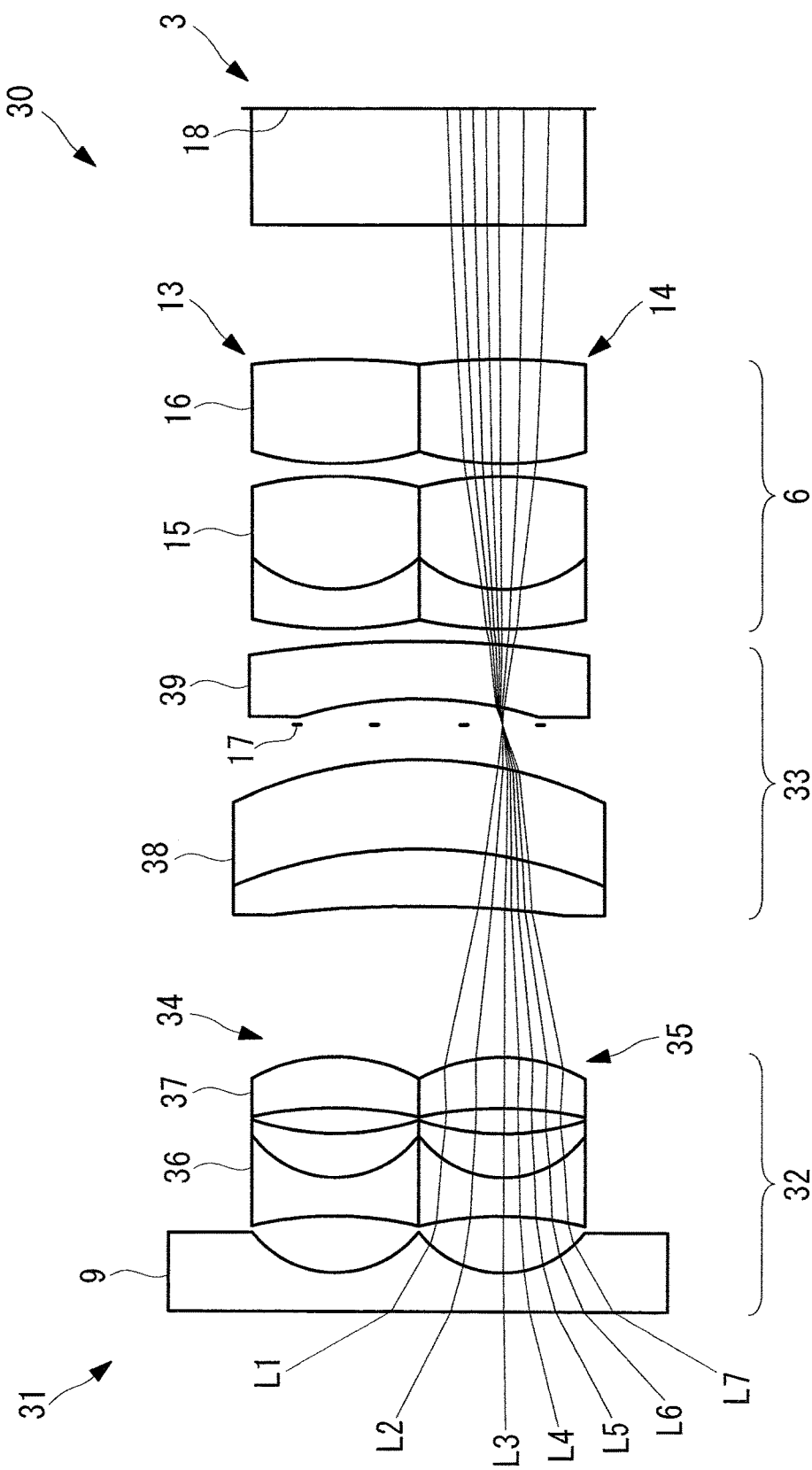
FIG. 20 is a view showing ray tracing of the principal ray when a moving lens group in an image acquisition device according to a third embodiment of the present invention is located at the far-point position.
Figure 21:
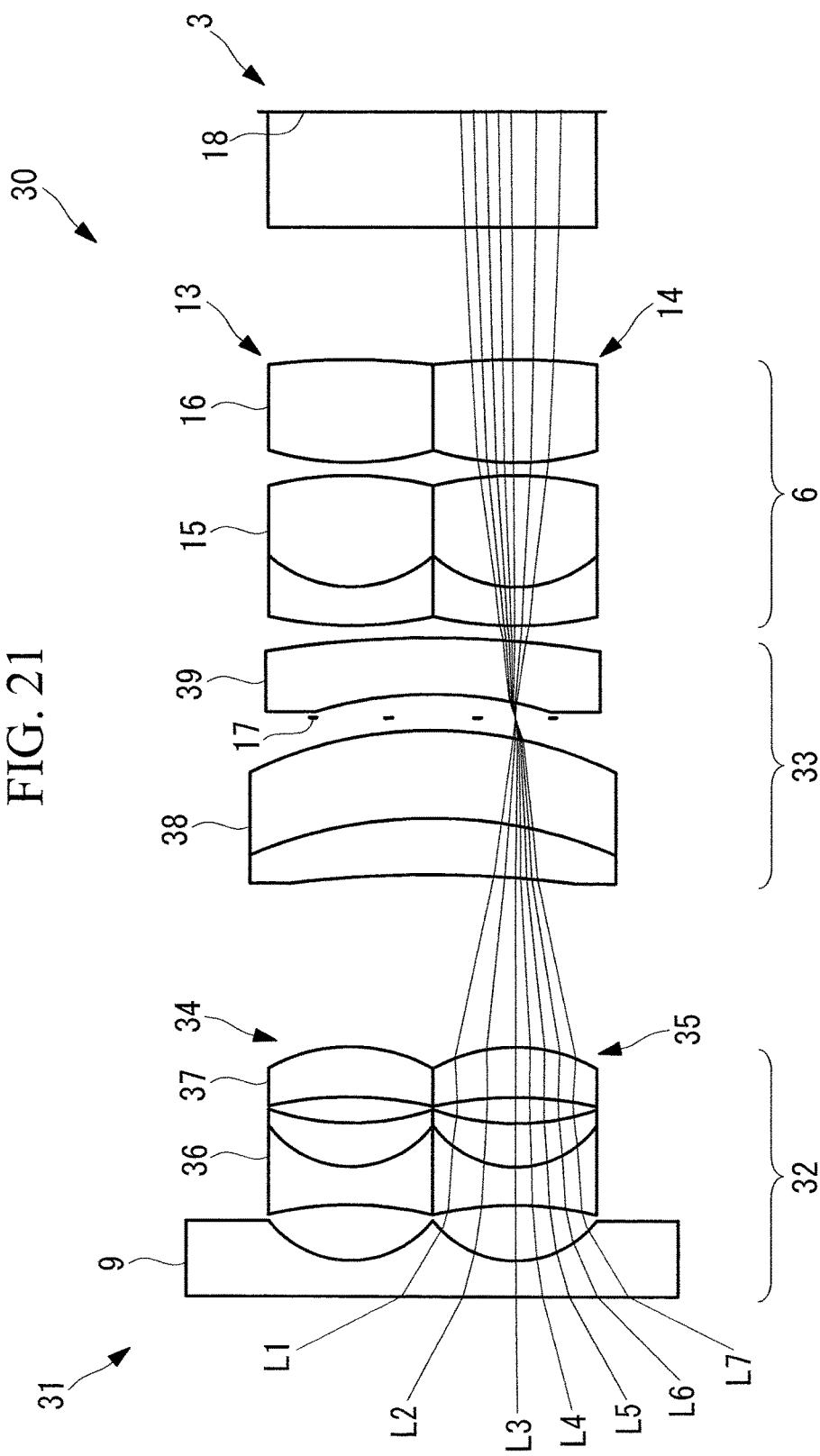
FIG. 21 is a view showing ray tracing of the principal ray when the moving lens in the image acquisition device shown in FIG. 20 is located at the near-point position.

As shown in FIGS. 20 and 21, this embodiment differs from the image acquisition device 20 of the second embodiment in terms of a first negative lens group 32 and a first positive lens group 33.

This embodiment differs from the image acquisition device 20 of the second embodiment in that two negative lens groups 34 and 35 in the first negative lens group 32 include: a combined lens 36 that is made up of a biconcave lens and a meniscus lens having a concave surface on the image side thereof; and one meniscus lens 37 that has a concave surface directed toward the object side.

Furthermore, this embodiment differs from the image acquisition device 20 of the second embodiment in that the first positive lens group 33 is provided with, in order from the object side: a combined lens 38 that is made up of two meniscus lenses having concave surfaces directed toward the object side; and one meniscus lens 39 that has a concave surface directed toward the object side.

Next, Example 4 of the image acquisition device 30 of this embodiment will be described below by using FIGS. 22 to 26 and lens data.

Figure 22:
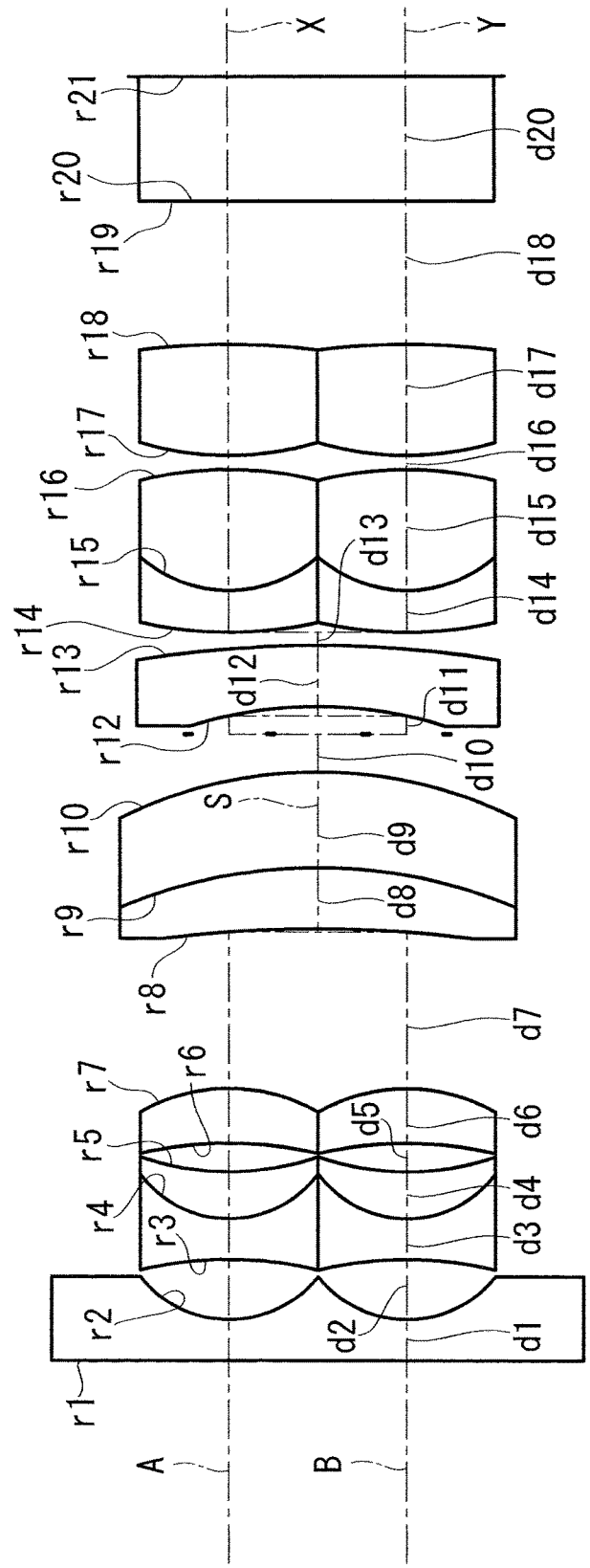
FIG. 22 is a view showing a lens array of an imaging optical system according to Example 4 of the image acquisition device shown in FIG. 20.
Figure 23:
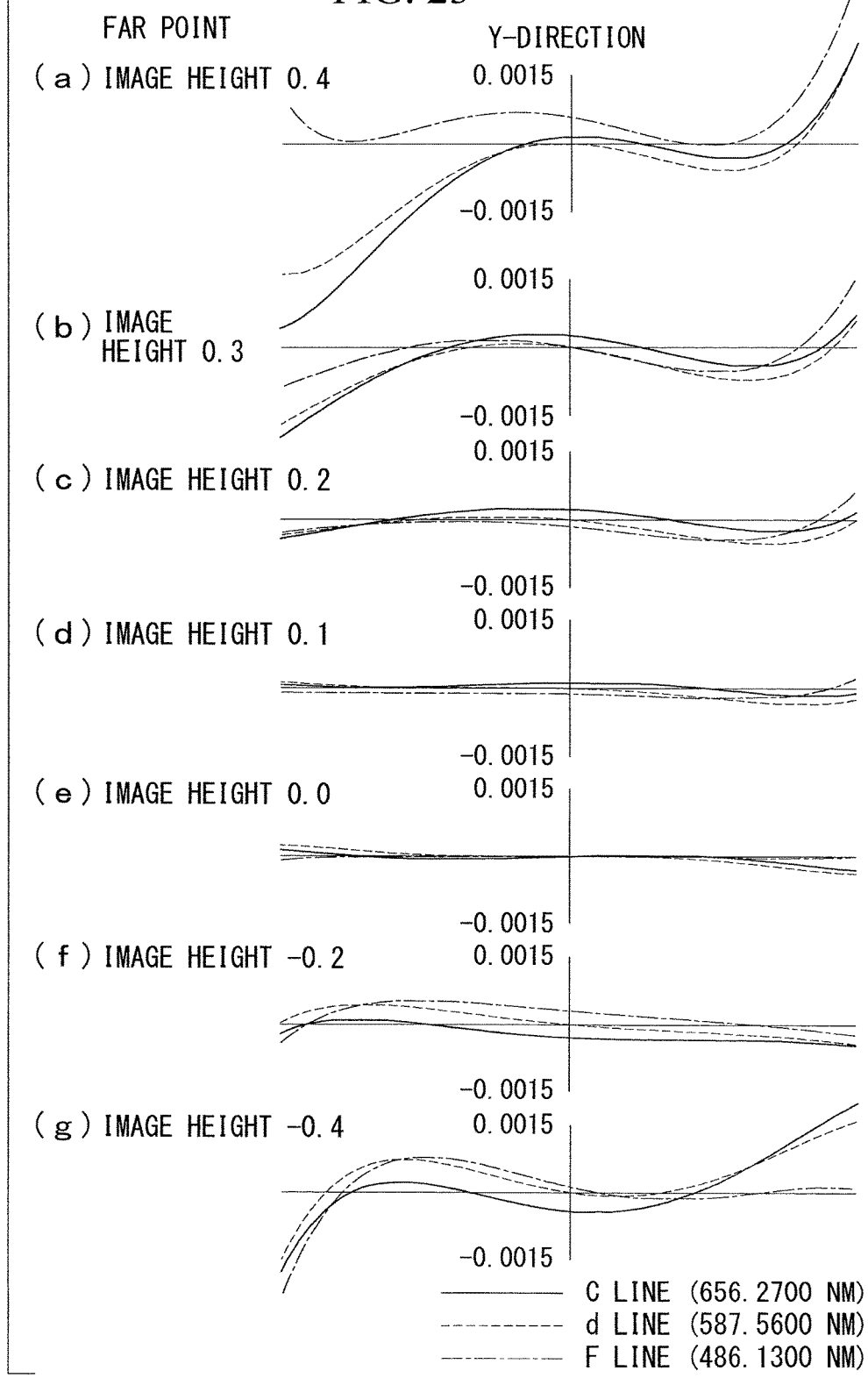
FIG. 23 is a view showing lateral aberrations of (a) the light ray L7, (b) the light ray L6, (c) the light ray L5, (d) the light ray L4, (e) the light ray L3, (f) the light ray L2, and (g) the light ray L1 in the Y-direction when the moving lens group in the imaging optical system shown in FIG. 22 is located at the far-point position shown in FIG. 20.
Figure 24:
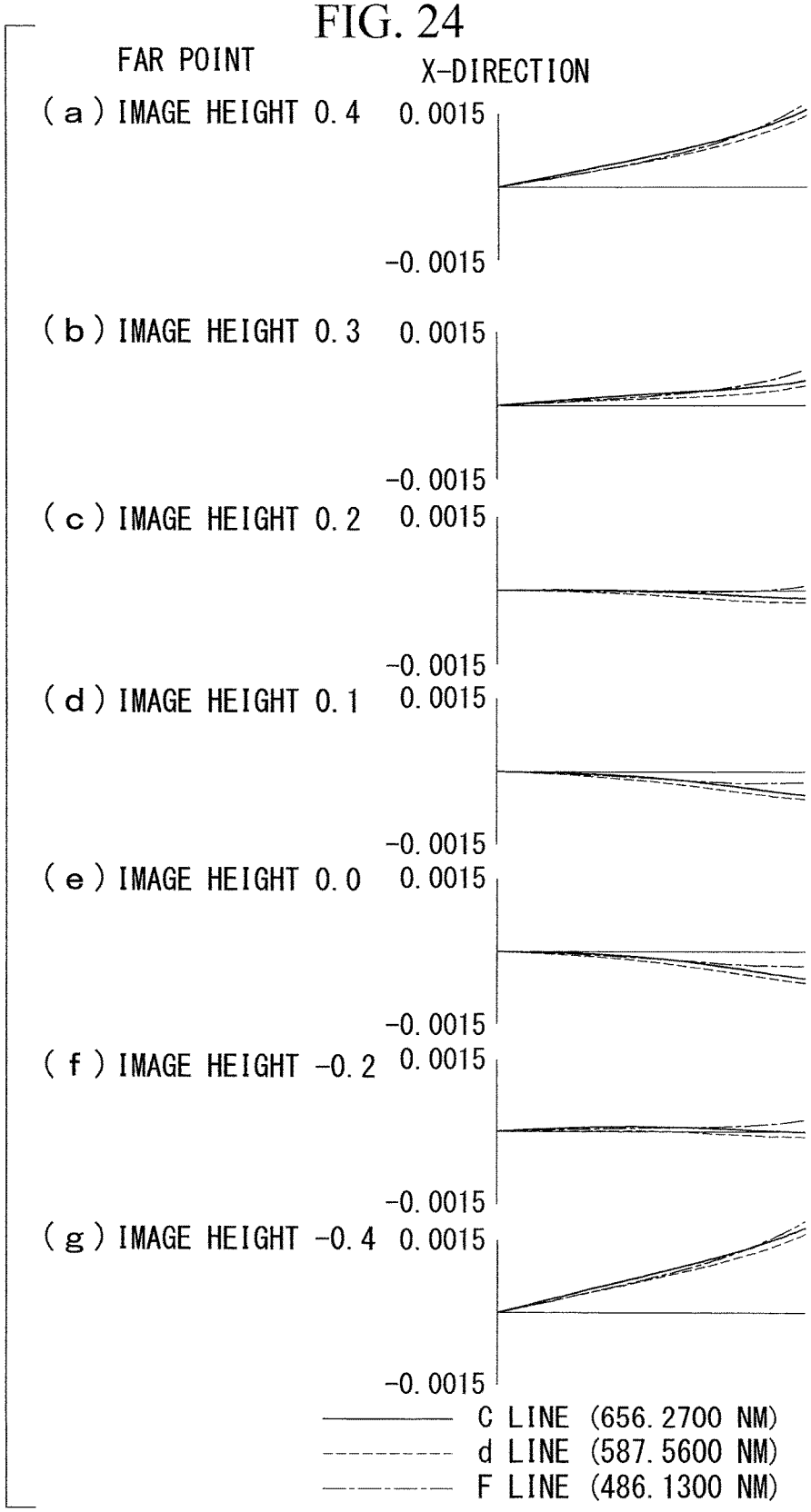
FIG. 24 is a view showing lateral aberrations of (a) the light ray L7, (b) the light ray L6, (c) the light ray L5, (d) the light ray L4, (e) the light ray L3, (f) the light ray L2, and (g) the light ray L1 in the X-direction when the moving lens group in the imaging optical system shown in FIG. 22 is located at the far-point position shown in FIG. 20.
Figure 25:
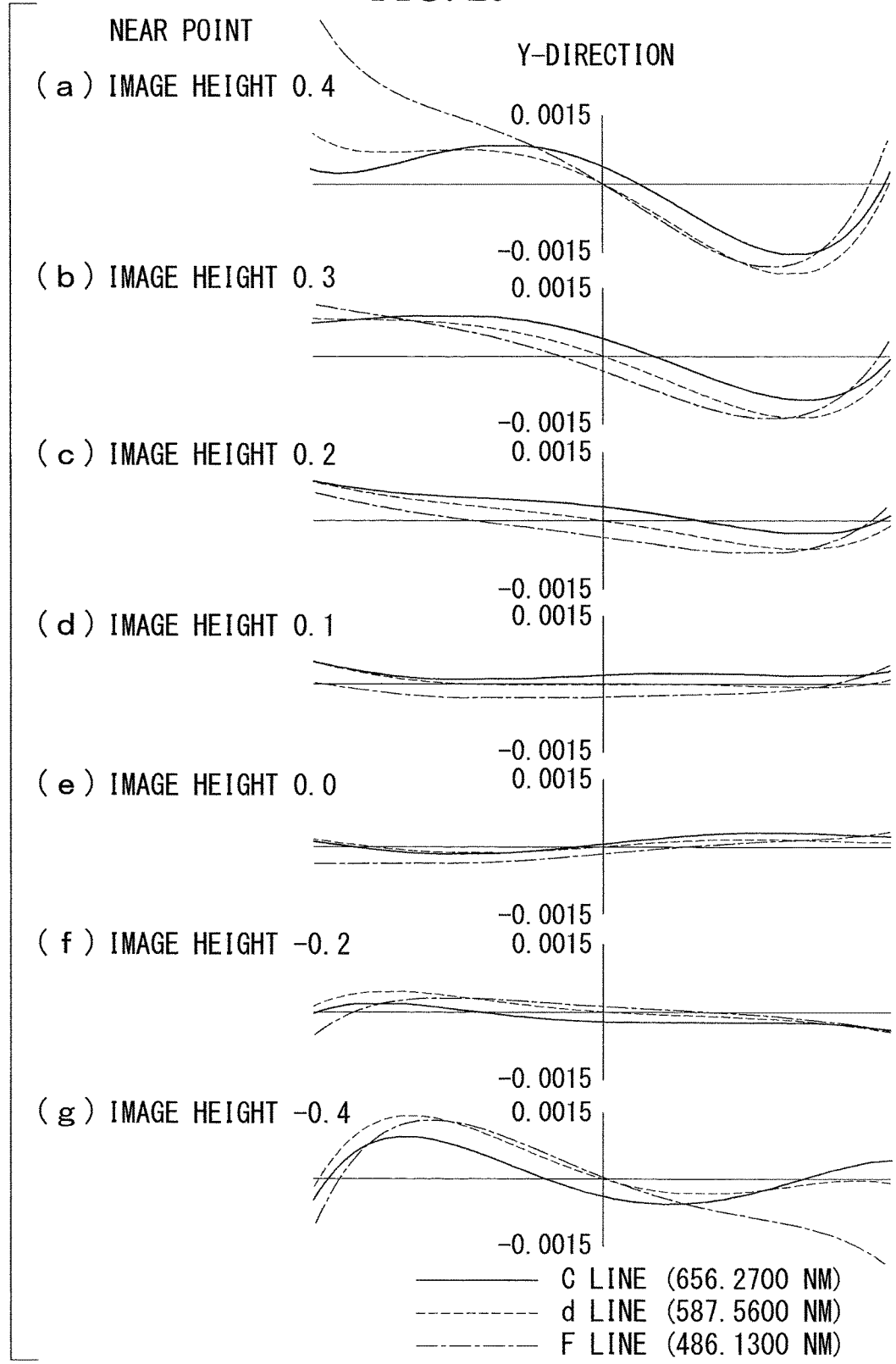
FIG. 25 is a view showing lateral aberrations of (a) the light ray L7, (b) the light ray L6, (c) the light ray L5, (d) the light ray L4, (e) the light ray L3, (f) the light ray L2, and (g) the light ray L1 in the Y-direction when the moving lens group in the imaging optical system shown in FIG. 22 is located at the near-point position shown in FIG. 21.
Figure 26:
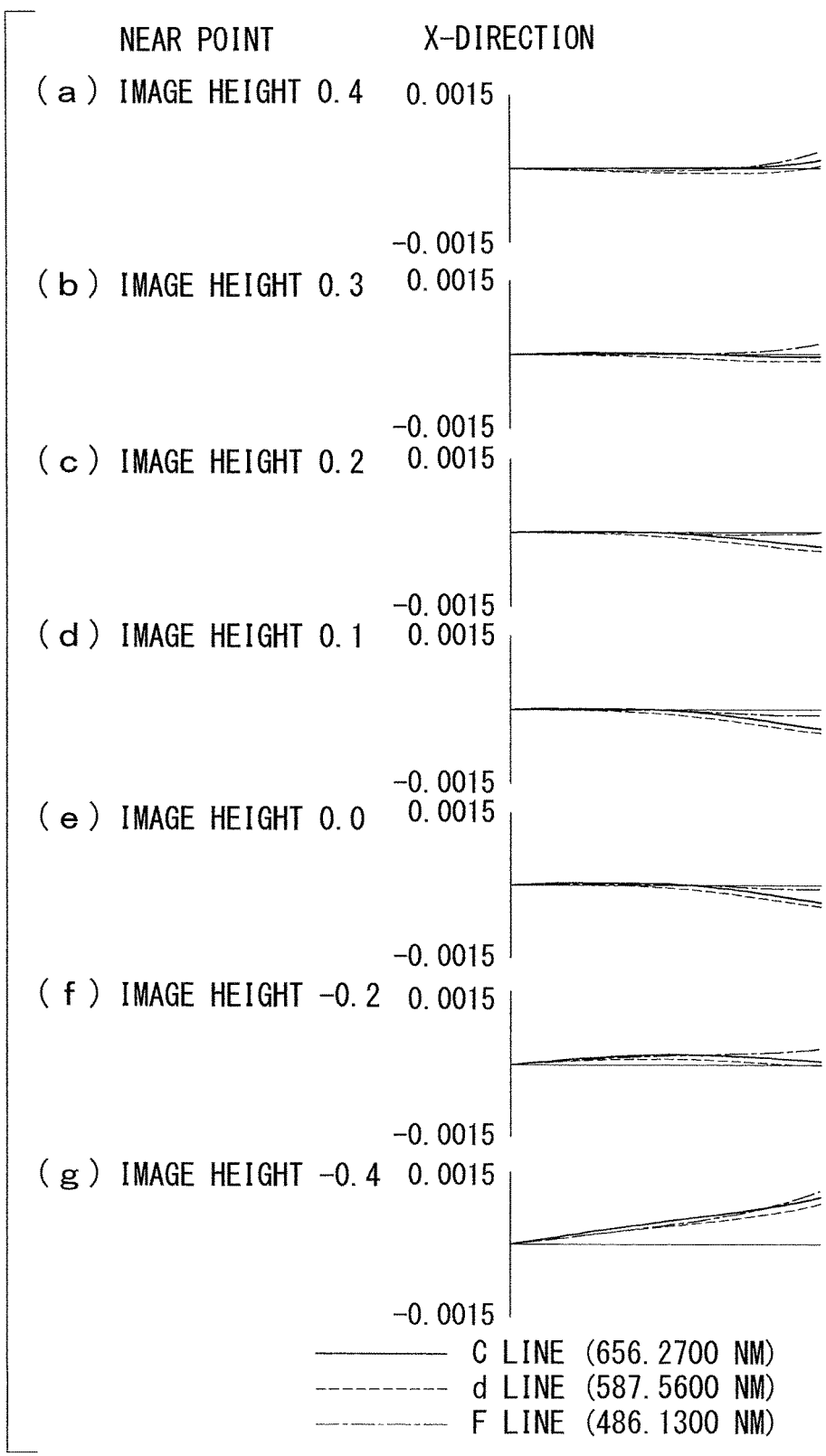
FIG. 26 is a view showing lateral aberrations of (a) the light ray L7, (b) the light ray L6, (c) the light ray L5, (d) the light ray L4, (e) the light ray L3, (f) the light ray L2, and (g) the light ray L1 in the X-direction when the moving lens group in the imaging optical system shown in FIG. 22 is located at the near-point position shown in FIG. 21.

FIG. 22 shows a lens array of an imaging optical system 31 of the image acquisition device 30 of this Example. Furthermore, FIGS. 23 to 26 are aberration diagrams corresponding to respective light rays L1 to L7 in the imaging optical system 31 of this Example.

In this Example, the maximum angle of view (far point) is 140°, the image height is 0.4 mm, and the Fno is 3.5.

| surface number | r | d | Nd | ν |
|---|---|---|---|---|
| OBJ | ∞ | 14 | | |
| 1 | ∞ | 0.3 | 1.74397 | 44.8496 |
| 2 | 0.75 | 0.45 | | |
| 3 | −2.50847 | 0.3 | 1.63854 | 55.3792 |
| 4 | 0.8 | 0.35 | 1.7552 | 27.579 |
| 5 | 1.99388 | 0.2 | | |
| 6 | −2.85914 | 0.4 | 1.7432 | 49.3387 |
| 7 | −1.30459 | 1.18951 | | |
| 8 | −11.2391 | 0.45 | 1.74077 | 27.7889 |
| 9 | −3.80255 | 0.7 | 1.62041 | 60.3227 |
| 10 | −3.27754 | 0.279688 | | |
| 11 | ∞ (stop) | 0.2 | | |
| 12 | −3.15044 | 0.45 | 1.74077 | 27.7889 |
| 13 | −8.88625 | 0.1 | | |
| 14 | 3.0047 | 0.3 | 1.75377 | 28.9881 |
| 15 | 1.00432 | 0.884321 | 1.58913 | 61.1341 |
| 16 | −2.43398 | 0.1 | | |
| 17 | 2.30107 | 0.817818 | 1.48749 | 70.2353 |
| 18 | −4.51289 | 1.05205 | | |
| 19 | ∞ (virtual plane) | 0 | | |
| 20 | ∞ | 0.9 | 1.51633 | 64.1411 |
| 21 | ∞ (imaging surface) | | | |

The object point, the inter-surface distance 7, and the inter-surface distance 10 in the above-described lens data show values obtained when the moving lens group 38 is located at the far-point position. Values obtained when the moving lens group 38 is located at the near-point position are: dOBJ (the distance from the object to the first surface)=4 mm; d7=1.3692 mm; and d10=0.1 mm.

Furthermore, the eleventh surface denotes the aperture stop 17, and the amounts of eccentricities yde in the eighth surface, the eleventh surface, the twelfth surface, the fourteenth surface, and the twenty-first surface with respect to the central axis S at the object sides thereof are:

eighth surface: yde=0.65 mm;
eleventh surface: yde=−0.65 mm;
twelfth surface: yde=0.65 mm;
fourteenth surface: yde=−0.65 mm; and
twenty-first surface: yde=0.024565 mm, respectively.

Table 1 shows values of conditions (1) to (4) in the above-described four Examples.

According to Table 1, the four Examples all satisfy conditions (1) to (4).

TABLE 1

| COMPUTATION EXPRESSION | | EXAMPLE 1 | EXAMPLE 2 | EXAMPLE 3 | EXAMPLE 4 |
|---|---|---|---|---|---|
| fm > (Dk × ΔD)/(ih × 0.2) | fm | 43.760 | 43.760 | 8.285 | 6.190 |
| | (Dk × ΔD)/(ih × 0.2) | 9.312 | 10.159 | 1.643 | 2.920 |
| −1.6 < fGN1/fGP2 < −0.6 | fGN1/fGP2 | −0.900 | −0.800 | −0.838 | −0.692 |
| −1.5 < Dk/fGN1 < 0 | Dk/fGN1 | −0.675 | −0.848 | −0.783 | −1.057 |
| 1 > Dk/fGP2 > 0 | Dk/fGP2 | 0.607 | 0.679 | 0.656 | 0.732 |

Application examples of the image acquisition device 1, 20, 30 of each of the embodiments of the present invention will be described below.

Figure 27:
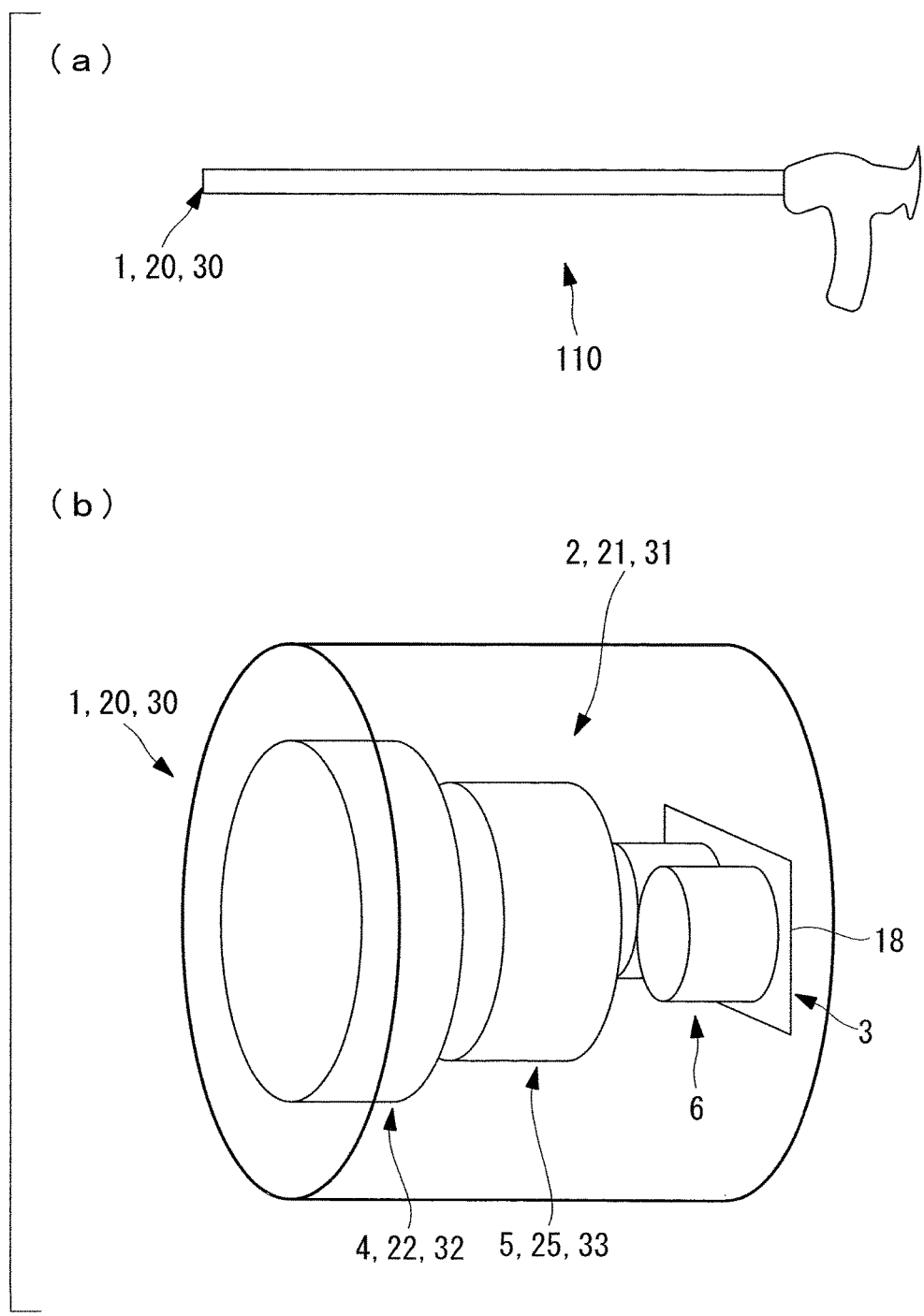
FIG. 27 includes (a) an overall view of a rigid endoscope to which the image acquisition device according to each of the embodiments is applied and (b) a perspective view showing a distal end portion thereof.

FIG. 27 includes views showing an example in which the image acquisition device 1, 20, 30 of each of the embodiments is applied to an endoscope. FIG. 27(a) is an overall view showing a rigid endoscope 110, and FIG. 27(b) shows the image acquisition device 1, 20, 30 of each of the embodiments attached to a distal end of the rigid endoscope 110.

Figure 28:
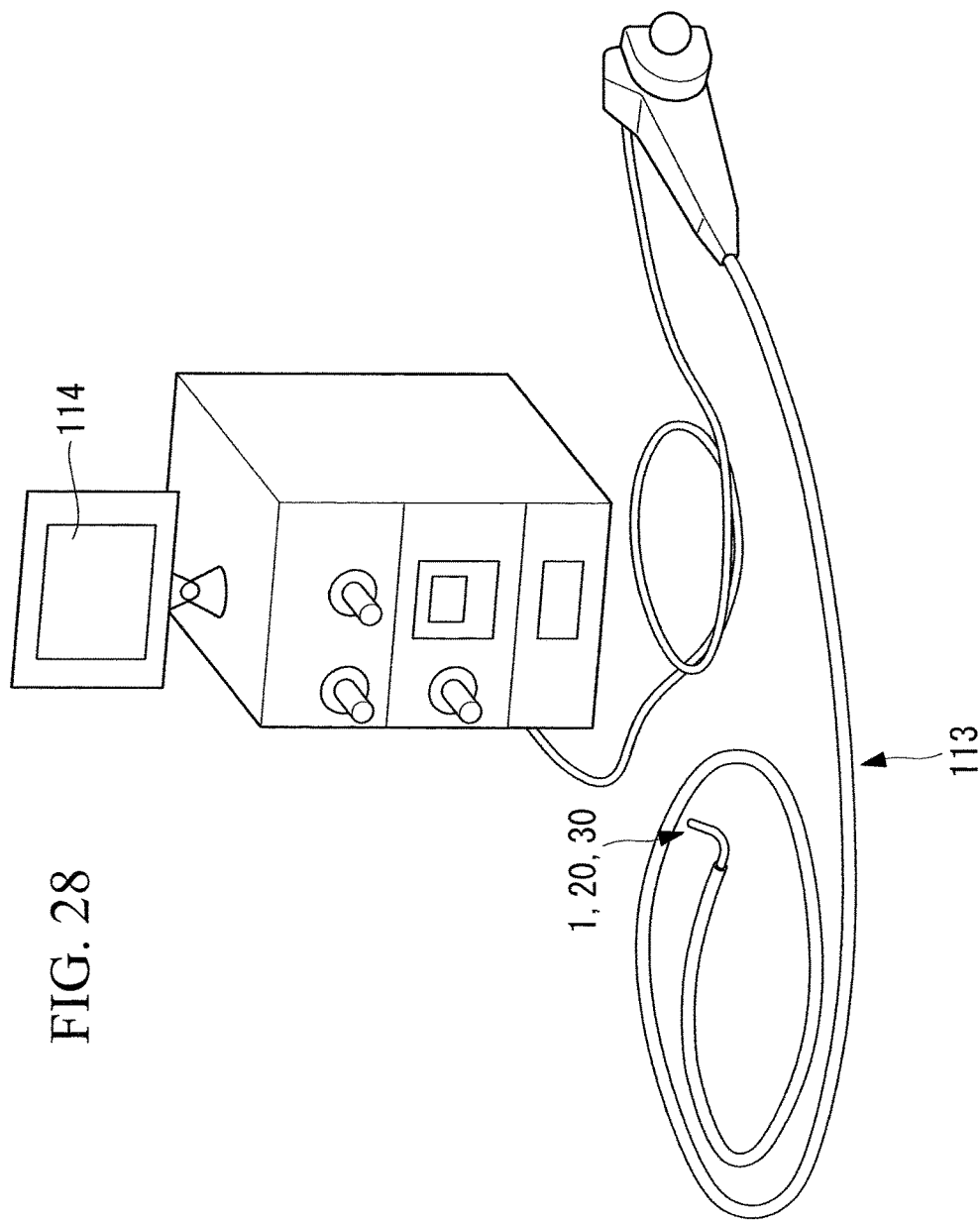
FIG. 28 is an overall view of a flexible electronic endoscope to which the image acquisition device according to each of the embodiments is applied.

Furthermore, FIG. 28 is an overall view showing a flexible-electronic-endoscope system. The image acquisition device 1, 20, 30 of each of the above-described embodiments is attached to a distal end of an insertion portion of a flexible electronic endoscope 113, and an acquired image is subjected to image processing to correct distortion and is stereoscopically displayed on a display device 114.

As shown in FIGS. 27 and 28, the image acquisition device 1, 20, 30 of each of the embodiments is applied to an endoscope, thereby making it possible to stereoscopically acquire and observe an omnidirectional image and to stereoscopically observe various sites from angles different from the conventional techniques.

Furthermore, FIG. 29 includes views showing an example in which the image acquisition device 1, 20, 30 of each of the embodiments of the present invention is applied to a vehicle 130.

As shown in FIGS. 29(a) and 29(b), the image acquisition device 1, 20, 30 is attached to respective portions of the vehicle 130, and acquired images are subjected to image processing to correct distortion and are stereoscopically displayed on a display device (not shown) in the vehicle at the same time.

From the above-described embodiments, the following aspects of the present invention are derived.

According to one aspect, the present invention provides an image acquisition device including: an imaging optical system that forms two images having parallax; and an image acquisition element that is disposed at an image side of the imaging optical system and that acquires the parallax images, wherein the imaging optical system is provided with a first negative lens group that has a negative refractive power, which are arranged in this order from an object side to an image side; a first positive lens group that has a positive refractive power, and a second positive lens group that has a positive refractive power; the first negative lens group is provided with two negative lens groups that are disposed side by side in a parallax direction corresponding to the parallax images and that have central axes respectively; the first positive lens group is a common lens group that has a single central axis and which light rays emitted from the respective negative lens groups in the first negative lens group to pass through; the second positive lens group is provided with two positive lens groups that are disposed side by side in the parallax direction corresponding to the parallax images and that have central axes respectively; and the first positive lens group is provided with a moving lens group that is moved along the central axis of the first positive lens group; wherein the image acquisition device further comprises an aperture stop that has openings corresponding to the respective parallax images and is disposed closer to an imaging surface than a lens surface of the first positive lens group, the lens surface being located closest to the first negative lens group; and central principal rays passing through the two negative lens groups reach the imaging surface without the principal rays intersecting.

According to this aspect, when light rays from an object enter the image acquisition device, two images having parallax are formed in the imaging optical system, and two parallax images are acquired by the image acquisition element. Because light rays from the object are focused by the first negative lens group, a wide angle of view can be secured, and the light fluxes individually focused by the two negative lens groups, which are disposed side by side in the parallax direction, corresponding to the parallax images are maintained at a small light-flux diameter by the first positive lens group, which is formed of a common lens group, located at the sequent stage. Then, the light rays that have passed through the first positive lens group again enter the second positive lens group, which is provided with the two positive lens groups disposed side by side in the parallax direction, thereby being respectively formed into two parallax images and acquired by the image acquisition element.

In this case, in order to adjust the focus position, the first positive lens group, which is disposed between the first negative lens group and the second positive lens group and which is the common lens group, is moved along the common central axis; therefore, it is not necessary to move the second positive lens group, which is close to the image acquisition element, thus making it possible to reduce the distance between the central axes of the two positive lens groups in the second positive lens group and to minimize the parallax. Furthermore, compared with a case in which the second positive lens group is moved, it is possible to reduce the impact of a driving error caused when the first positive lens group is moved along the common central axis and to minimize the incident angles at the image acquisition element, thus making it possible to suppress a reduction in detection sensitivity.

In the above-described aspect, the moving lens group may be provided with combined lens component including a positive lens that has a positive refractive power and a negative lens that has a negative refractive power.

By doing so, it is possible to suppress chromatic aberration through driving of the moving lens group, which is provided with the combined lens components.

Furthermore, in the above-described aspect, the first positive lens group may be provided with a plurality of lens groups that are disposed side by side with a space which is variable.

Furthermore, in the above-described aspect, the first positive lens group may be provided with a positive lens group that has a positive refractive power and a negative lens group that has a negative refractive power.

By doing so, a shift of the optical axis in the common lens can be suppressed by means of a combination of concavity and convexity.

Furthermore, in the above-described aspect, the distance between the positive lens group and the negative lens group in the first positive lens group may vary.

Furthermore, in the above-described aspect, the positive lens group in the first positive lens group may be a moving lens group; and the negative lens group may be statically disposed on an image side of the positive lens group.

Furthermore, in the above-described aspect, the moving lens group may satisfy condition (1):

$$fm > (Dk \times \Delta D)/(ih \times 0.2) \quad (1)$$

wherein fm indicates an absolute value of a focal length of the moving lens group, $\Delta D$ indicates a maximum amount of movement of the moving lens group, ih indicates an image height of the parallax image, and Dk indicates a distance between the central axes in the second positive lens group.

By doing so, it is possible to suppress aberration caused by a lens driving error.

Furthermore, in the above-described aspect, the imaging optical system may be provided with an aperture stop that has openings corresponding to the respective parallax images; and a center of any one of the openings of the aperture stop may be eccentric with respect to the central axis of the corresponding negative lens group in the first negative lens group.

By doing so, even when the entrance pupil positions are close together, the imaging positions of the parallax images can be shifted, thus making it possible to reduce vignetting of the light fluxes.

Furthermore, in the above-described aspect, distance between the centers of the plurality of openings may be larger than distance between the central axes of the corresponding negative lens groups in the first negative lens group.

By doing so, it is possible to reduce crosstalk of the parallax images obtained when the imaging angle of view is increased.

Furthermore, in the above-described aspect, distance between the centers of the plurality of openings may be smaller than distance between the central axes of the corresponding negative lens groups in the first negative lens group.

By doing so, the distance between the parallax images is reduced, thus making it possible to reduce the size of the imaging surface of the image acquisition element.

Furthermore, in the above-described aspect, the imaging optical system may be provided with an aperture stop that has openings corresponding to the respective parallax images; the first positive lens group may have a plurality of lens groups; and the openings may be located in the plurality of lens groups in the first positive lens group.

By doing so, it is possible to suppress both the effective diameter of the first negative lens group and the effective diameter of the second positive lens group and to reduce the impact of vignetting. Even when the distance between the pupils of the negative lens groups in the first negative lens group is not increased, it is possible to acquire parallax images with a wide angle of view and to achieve a reduction in size.

Furthermore, in the above-described aspect, the image acquisition device may satisfy condition (2);

$$-1.6 < fGN1/fGP2 < -0.6 \quad (2)$$

wherein fGN1 indicates a focal length of the first negative lens group, and fGP2 indicates a focal length of the second positive lens group.

By doing so, the ratio of the focal length of the first negative lens group and the focal length of the second positive lens group is set close to −1, and the magnification at the first positive lens group, which is disposed between the first negative lens group and the second positive lens group and which is the common lens group, is set around −1, thus making it possible to reduce a fluctuation in aberration when the moving lens group is moved.

Furthermore, in the above-described aspect, the image acquisition device may satisfy condition (3);

$$-1.5 < Dk/fGN1 < 0 \quad (3)$$

wherein fGN1 indicates a focal length of the first negative lens group, and Dk indicates a distance between the central axes in the second positive lens group.

Furthermore, in the above-described aspect, the image acquisition device may satisfy condition (4);

$$1 > Dk/fGP2 > 0 \quad (4)$$

wherein fGP2 indicates a focal length of the second positive lens group, and Dk indicates a distance between the central axes in the second positive lens group.

The aforementioned aspects afford an advantageous effect in that it is possible to suppress an increase in parallax, to reduce the angles of incidence of light rays on an image acquisition element, and to acquire a clear image.

REFERENCE SIGNS LIST 1, 20, 30 image acquisition device
2, 21, 31 imaging optical system
3 image acquisition element
4, 22, 32 first negative lens group
5, 25, 33 first positive lens group (moving lens group)
6 second positive lens group
7, 8, 23, 24, 34, 35 negative lens group
13, 14 positive lens group
17 aperture stop (stop)
A, B, S, X, Y central axis

The invention claimed is:

1. An image acquisition device comprising:
   an imaging optical system that forms two images having parallax; and
   an image acquisition element that is disposed at an image side of the imaging optical system and that acquires the parallax images,
   wherein:
   the imaging optical system is provided with a first negative lens group that has a negative refractive power, a first positive lens group that has a positive refractive power, and a second positive lens group that has a positive refractive power, which are arranged in this order from an object side to an image side;
   the first negative lens group is provided with two negative lens groups that are disposed side by side in a parallax direction corresponding to the parallax images and that have central axes respectively;
   the first positive lens group is a common lens group that has a single central axis and which light rays emitted from the respective negative lens groups in the first negative lens group pass through;
   the second positive lens group is provided with two positive lens groups that are disposed side by side in the parallax direction corresponding to the parallax images and that have central axes respectively;
   the first positive lens group is provided with a moving lens group that is moved along the central axis of the first positive lens group;
   the image acquisition device further comprises an aperture stop that has openings corresponding to the respective parallax images and is disposed closer to an imaging surface than a lens surface of the first positive lens group, the lens surface being located closest to the first negative lens group; and
   central principal rays passing through the two negative lens groups reach the imaging surface without the principal rays intersecting.

2. The image acquisition device according to claim 1, wherein the moving lens group is provided with combined lens components including a positive lens that has a positive refractive power and a negative lens that has a negative refractive power.

3. The image acquisition device according to claim 1, wherein the first positive lens group is provided with a plurality of lens groups that are disposed side by side with a space which is variable.

4. The image acquisition device according to claim 1, wherein the first positive lens group is provided with a positive lens group that has a positive refractive power and a negative lens group that has a negative refractive power.

5. The image acquisition device according to claim 4, wherein a distance between the positive lens group and the negative lens group in the first positive lens group is variable.

6. The image acquisition device according to claim 5, wherein:
   the positive lens group in the first positive lens group is a moving lens group; and
   the negative lens group in the first positive lens group is statically disposed on an image side of the positive lens group in the first positive lens group.

7. The image acquisition device according to claim 1, wherein the moving lens group satisfies a condition (1); (1):

$$fm > (Dk \times \Delta D)/(ih \times 0.2) \tag{1}$$

wherein:
fm indicates an absolute value of a focal length of the moving lens group,
$\Delta D$ indicates a maximum amount of movement of the moving lens group,
ih indicates an image height of the parallax image, and
Dk indicates a distance between the central axes of the two positive lens groups in the second positive lens group.

8. The image acquisition device according to claim 1, wherein:
   the imaging optical system is provided with an aperture stop that has openings corresponding to the respective parallax images; and
   a center of one of the openings of the aperture stop is eccentric with respect to the central axis of its corresponding negative lens group in the first negative lens group.

9. The image acquisition device according to claim 8, wherein a distance between the centers of the plurality of openings is larger than a distance between the central axes of the corresponding negative lens groups in the first negative lens group.

10. The image acquisition device according to claim 8, wherein a distance between the centers of the plurality of openings is smaller than a distance between the central axes of the corresponding negative lens groups in the first negative lens group.

11. The image acquisition device according to claim 1, wherein:
    the imaging optical system is provided with an aperture stop that has openings corresponding to the respective parallax images;
    the first positive lens group has a plurality of lens groups; and
    the openings are located in the plurality of lens groups in the first positive lens group.

12. The image acquisition device according to claim 1, wherein the image acquisition device satisfies a condition (2); (2):

$$-1.6 < fGN1/fGP2 < -0.6 \tag{2}$$

wherein:
fGN1 indicates a focal length of the first negative lens group, and
fGP2 indicates a focal length of the second positive lens group.

13. The image acquisition device according to claim 1, wherein the image acquisition device satisfies a condition (3); (3):

$$-1.5 < Dk/fGN1 < 0 \tag{3}$$

wherein:
fGN1 indicates a focal length of the first negative lens group, and
Dk indicates a distance between the central axes in the second positive lens group.

14. The image acquisition device according to claim 1, wherein the image acquisition device satisfies a condition (4); (4):

$$1 > Dk/fGP2 > 0 \tag{4}$$

wherein:
fGP2 indicates a focal length of the second positive lens group, and
Dk indicates a distance between the central axes of the two positive lens groups in the second positive lens group.

15. An endoscope comprising:
- an imaging optical system that forms two images having parallax; and
- an image acquisition element that is disposed at an image side of the imaging optical system and that acquires the parallax images, wherein:
- the imaging optical system is provided with a first negative lens group that has a negative refractive power, a first positive lens group that has a positive refractive power, and a second positive lens group that has a positive refractive power, which are arranged in this order from an object side to an image side;
- the first negative lens group is provided with two negative lens groups that are disposed side by side in a parallax direction corresponding to the parallax images and that have central axes respectively;
- the first positive lens group is a common lens group that has a single central axis and which light rays emitted from the respective negative lens groups in the first negative lens group pass through;
- the second positive lens group is provided with two positive lens groups that are disposed side by side in the parallax direction corresponding to the parallax images and that have central axes respectively; and
- the first positive lens group is provided with a moving lens group that is moved along the central axis of the first positive lens group.

* * * * *